(12) United States Patent
Edmunds et al.

(10) Patent No.: US 10,196,398 B2
(45) Date of Patent: Feb. 5, 2019

(54) PESTICIDALLY ACTIVE TETRACYCLIC DERIVATIVES WITH SULFUR CONTAINING SUBSTITUENTS

(71) Applicant: Syngenta Participations AG, Basel (CH)

(72) Inventors: Andrew Edmunds, Stein (CH); Pierre Joseph Marcel Jung, Stein (CH); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/540,057

(22) PCT Filed: Dec. 15, 2015

(86) PCT No.: PCT/EP2015/079877
§ 371 (c)(1),
(2) Date: Jun. 27, 2017

(87) PCT Pub. No.: WO2016/107742
PCT Pub. Date: Jul. 7, 2016

(65) Prior Publication Data
US 2018/0009813 A1 Jan. 11, 2018

(30) Foreign Application Priority Data
Dec. 29, 2014 (EP) .................... 14200413

(51) Int. Cl.
*C07D 487/04* (2006.01)
*A01N 43/90* (2006.01)
*C07D 471/04* (2006.01)

(52) U.S. Cl.
CPC .......... *C07D 487/04* (2013.01); *A01N 43/90* (2013.01); *C07D 471/04* (2013.01)

(58) Field of Classification Search
CPC .................................................. C07D 487/04
See application file for complete search history.

(56) References Cited

FOREIGN PATENT DOCUMENTS

| WO | 2012086848 A1 | 6/2012 |
| WO | 2013018928 A1 | 2/2013 |
| WO | 2013191113 A1 | 12/2013 |

OTHER PUBLICATIONS

Vippagunta et al. (2001).*
Extended European Search Report for 14200413.4 dated Mar. 30, 2015.
International Search Report and Written Opinion for PCT/EP2015/079877, dated Feb. 1, 2016.

* cited by examiner

*Primary Examiner* — Paul V Ward
(74) *Attorney, Agent, or Firm* — Dinsmore & Shohl LLP; Toni-Junnell Herbert

(57) ABSTRACT

Compounds of formula I, wherein the substituents are as defined in claim 1, and the agrochemically acceptable salts, stereoisomers, enantiomers, tautomers and N-oxides of those compounds, can be used as insecticides and can be prepared in a manner known per se.

14 Claims, No Drawings

PESTICIDALLY ACTIVE TETRACYCLIC DERIVATIVES WITH SULFUR CONTAINING SUBSTITUENTS

RELATED APPLICATION INFORMATION

This application is a 371 of International Application No. PCT/EP2015/079877, filed 15 Dec. 2015, which claims priority to EP 14200413.4, filed 29 Dec. 2014, the contents of which are incorporated herein by reference herein.

The present invention relates to pesticidally active, in particular insecticidally active tetracyclic derivatives containing sulfur substituents, to compositions comprising those compounds, and to their use for controlling animal pests (including arthropods and in particular insects or representatives of the order Acarina).

Heterocyclic compounds with pesticidal action are known and described, for example, in WO 2012/086848, WO 2013/018928 and WO 2013/191113.

There have now been found novel pesticidally active tetracyclic derivatives with a sulfur containing bicyclic moiety.

The present invention accordingly relates to compounds of formula I,

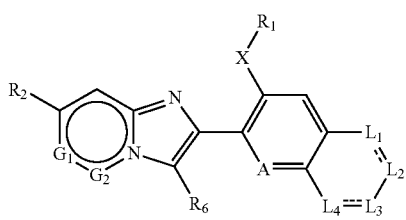

(I)

wherein

A is CH or N;

X is S, SO or $SO_2$;

$R_1$ is $C_1$-$C_4$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano, $C_1$-$C_4$haloalkyl and $C_1$-$C_4$alkyl; or is $C_3$-$C_6$cycloalkyl-$C_1$-$C_4$alkyl mono- or polysubstituted by substituents selected from the group consisting of halogen, cyano, $C_1$-$C_4$ haloalkyl and $C_1$-$C_4$alkyl;

$R_2$ is hydrogen, halogen, $C_1$-$C_4$haloalkylsulfanyl, $C_1$-$C_4$haloalkylsulfinyl, $C_1$-$C_4$haloalkylsulfonyl, $O(C_1$-$C_4$haloalkyl), —$SF_5$, —$C(O)C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$haloalkyl and $C_1$-$C_4$alkyl;

$G_1$ is N or $CR_4$;

$G_2$ is N or $CR_5$, with the proviso that when $G_1$ is N, $G_2$ is $CR_5$;

$R_6$ is hydrogen, halogen or $C_1$-$C_4$alkyl;

$R_4$ and $R_5$, independently from each other, are hydrogen, halogen, cyano, nitro, $C_1$-$C_6$alkyl, $C_1$-$C_6$haloalkyl, or are $C_3$-$C_6$cycloalkyl which can be mono- or polysubstituted by $R_8$; or are $C_3$-$C_6$cycloalkyl-$C_1$-$C_4$alkyl which can be mono- or polysubstituted by $R_9$; or $R_4$ and $R_5$, independently from each other, are $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl $C_1$-$C_6$haloalkylsulfanyl, $C_1$-$C_4$haloalkylsulfonyl, $C_1$-$C_6$haloalkylsulfinyl or hydroxyl; $R_8$ and $R_9$, independently from each other, are halogen, nitro, cyano, $C_1$-$C_4$haloalkoxy, $C_1$-$C_4$alkoxy $C_1$-$C_4$alkyl or $C_1$-$C_4$haloalkyl; and $L_1$, $L_2$, $L_3$ and $L_4$ form together with the two carbon atoms to which $L_1$ and $L_4$ are attached, an aromatic, partially saturated carbocyclic or heterocyclic ring system; wherein $L_1$ is nitrogen, S(O)n, oxygen, N—$R_{10a}$ or $C(R_{10a})_m$;

$L_2$ is nitrogen, S(O)n, oxygen, N—$R_{10b}$, or $C(R_{10b})_m$;

$L_3$ is nitrogen, S(O)n, oxygen, N—$R_{10c}$, or $C(R_{10c})_m$;

$L_4$ is nitrogen, S(O)n, oxygen, a direct bond, N—$R_{10d}$ or $C(R_{10d})_m$; with the provisos that no more than 2 substituents selected from $L_1$, $L_2$, $L_3$ and $L_4$ can be oxygen or sulfur; and if two L groups are oxygen, they are not adjacent to each other; and no more than three L groups can be nitrogen;

n is 0 to 2;

m is 1 or 2;

$R_{10a}$, $R_{10b}$, $R_{10c}$, and $R_{10d}$, independently from each other, are hydrogen, halogen, nitro, cyano, amino, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_4$alkoxy $C_1$-$C_4$alkyl, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_2$-$C_6$alkylcarbonyl, $C_2$-$C_6$alkoxycarbonyl, $C_2$-$C_6$ haloalkylcarbonyl, $C_2$-$C_6$haloalkoxycarbonyl, ($C_1$-$C_6$alkyl)NH, ($C_1$-$C_6$alkyl)$_2$N, ($C_1$-$C_6$cycloalkyl)NH, ($C_1$-$C_6$cycloalkyl)$_2$N, $C_1$-$C_6$alkylcarbonylamino, $C_1$-$C_6$cycloalkylcarbonylamino or —$SF_5$; additionally one of $R_{10a}$, $R_{10b}$, $R_{10c}$ and $R_{10d}$ can be oxo; or $R_{10a}$, $R_{10b}$, $R_{10c}$, and $R_{10d}$, independently from each other, are $C_3$-$C_6$cycloalkyl mono- or polysubstituted by substituents selected from the group consisting of $C_1$-$C_4$ haloalkyl, $C_1$-$C_4$alkyl and cyano; or $R_{10a}$, $R_{10b}$, $R_{10c}$, and $R_{10d}$, independently from each other, are phenyl which can be mono- or polysubstituted by substituents selected from the group consisting of halogen, $C_1$-$C_4$ haloalkyl, $C_1$-$C_4$alkyl, $C_1$-$C_4$alkoxy and cyano; and agrochemically acceptable salts, stereoisomers, enantiomers, tautomers and N-oxides of those compounds.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

m is 1 or 2 depending on the hybridization of the carbon atom.

If m is 2 in the definition $C(R_{10a})_m$, $R_{10a}$ can be the same or different; for example one $R_{10a}$ can be hydrogen and the other methyl. This is also valid for the definitions of $C(R_{10b})_m$, $C(R_{10c})_m$ and $C(R_{10d})_m$. The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_4$ alkynyl" and "$C_2$-$C_3$alkynyl" are to be construed accordingly. Examples of $C_2$-$C_6$alkynyl include, but are not limited to, ethynyl, prop-1-ynyl, but-1-ynyl, but-2-ynyl.

As used herein, the term "$C_2$-$C_6$alkenyl" refers to a straight or branched hydrocarbon chain radical group consisting solely of carbon and hydrogen atoms, containing at least one double bond, having from two to six carbon atoms, and which is attached to the rest of the molecule by a single bond. The term "$C_2$-$C_4$ alkenyl" and "$C_2$-$C_3$alkenyl" are to be construed accordingly. Examples of $C_2$-$C_6$alkenyl include, but are not limited to, prop-1-enyl, but-1-enyl, but-2-enyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is bond, an aromatic, partially saturated carbocyclic ring system, the carbocyclic ring system is preferably a group having 5 to 6 ring carbon atoms which are unsaturated or partially saturated, for example, but are not limited to phenyl and cyclohexenyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is bond, an aromatic or partially saturated heterocyclic ring system", the heterocyclic ring system is preferably a group comprising 1 to 3 heteroatoms in the ring, which are unsaturated or partially saturated, for example, but are not limited to pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl; pyranyl; pyrrolidinyl; piperidinyl; pyrrolidinyl-2-one; piperidinyl-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

An example for an aromatic or partially saturated carbocyclic or heterocyclic ring system wherein one of $R_{10a}$, $R_{10b}$, $R_{10c}$ or $R_{10d}$ can represent oxo, is the group $J_{15}$:

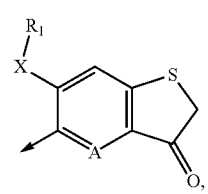

wherein X, $R_1$ and A are as defined under formula I above.

The compounds of formula I according to the invention also include hydrates which may be formed during the salt formation.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is bond, an aromatic, partially saturated or fully saturated carbocyclic ring system", the carbocyclic ring system is preferably a group having 5 to 6 ring carbon atoms which are saturated, unsaturated or partially saturated, for example phenyl, cyclopentyl and cyclohexenyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is bond, an aromatic, partially saturated or fully saturated heterocyclic ring system", the heterocyclic ring system is preferably a group having 5 to 6 ring carbon atoms which are saturated, unsaturated or partially saturated, for example pyrazole, pyrrole, pyrrolidine, pyrrolidine-2-one, imidazole, triazole and pyridine-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

An example for an aromatic, partially saturated or fully saturated carbocyclic or heterocyclic ring system wherein one of $R_{10a}$, $R_{10b}$, $R_{10c}$ or $R_{10d}$ can represent oxo, is the group $J_{15}$:

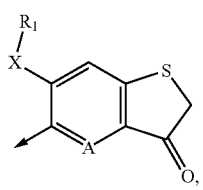

wherein X, $R_1$ and A are as defined under formula I above.

The compounds of formula I according to the invention also include hydrates which may be formed during the salt formation.

Preferred compounds of formula I are are those, wherein $R_1$ is $C_1$-$C_4$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl or $C_3$-$C_6$cycloalkyl-$C_1$-$C_4$alkyl; or $R_1$ is $C_3$-$C_6$cycloalkyl mono- or polysubstituted by substituents selected from the group consisting of halogen, cyano and $C_1$-$C_4$alkyl; or is $C_3$-$C_6$cycloalkyl-$C_1$-$C_4$alkyl mono- or polysubstituted by substituents selected from the group consisting of halogen, cyano and $C_1$-$C_4$alkyl;

$R_2$ is hydrogen, halogen, $C_1$-$C_4$haloalkylsulfanyl, $C_1$-$C_4$haloalkylsulfinyl, $C_1$-$C_4$haloalkylsulfonyl, O($C_1$-$C_4$haloalkyl), —$SF_5$, —C(O)$C_1$-$C_4$haloalkyl, cyano or $C_1$-$C_6$haloalkyl; or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano and $C_1$-$C_4$alkyl;

$G_1$ is N or $CR_4$;

$G_2$ is N or $CR_5$, with the proviso that when $G_1$ is N, $G_2$ is $CR_5$;

$R_6$ is hydrogen, halogen or $C_1$-$C_4$alkyl;

$R_4$ and $R_5$, independently from each other, are hydrogen, halogen, cyano, nitro, $C_1$-$C_6$alkyl, $C_1$-$C_6$haloalkyl, or are $C_3$-$C_6$cycloalkyl which can be mono- or polysubstituted by $R_8$; or are $C_3$-$C_6$cycloalkyl-$C_1$-$C_4$alkyl which can be mono- or polysubstituted by $R_9$; or $R_4$ and $R_5$, independently from each other, are $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl $C_1$-$C_6$haloalkylsulfanyl, $C_1$-$C_4$haloalkylsulfonyl, $C_1$-$C_6$haloalkylsulfinyl or hydroxyl;

$R_8$ and $R_9$, independently from each other, are halogen, nitro, cyano, $C_1$-$C_4$haloalkoxy, $C_1$-$C_4$alkoxy $C_1$-$C_4$alkyl or $C_1$-$C_4$haloalkyl; and $L_1$, $L_2$, $L_3$ and $L_4$ form together with the two carbon atoms to which $L_1$ and $L_4$ are attached, an aromatic or partially saturated carbocyclic or heterocyclic ring system; wherein $L_1$ is nitrogen, sulfur, oxygen or C—$R_{10a}$;

$L_2$ is nitrogen, sulfur, oxygen or C—$R_{10b}$;

$L_3$ is nitrogen, sulfur, oxygen or C—$R_{10c}$;

$L_4$ is nitrogen, sulfur, oxygen, a direct bond or C—$R_{10d}$; with the provisos that no more than 2 substituents selected from $L_1$, $L_2$, $L_3$ and $L_4$ can be oxygen or sulfur; and if two L groups are oxygen, they are not adjacent to each other;

$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl or —$SF_5$; additionally one of $R_{10a}$, $R_{10b}$, $R_{10c}$ and $R_{10d}$ can be oxo; and agrochemically acceptable salts, stereoisomers, enantiomers, tautomers and N-oxides of those compounds.

A preferred group of compounds of formula I is represented by the compounds of formula I-1

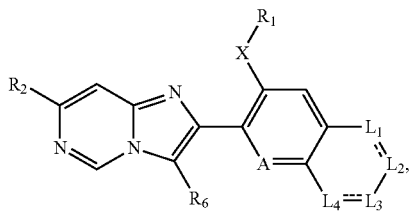

(I-1)

wherein the substituents X, A, R₁, R₂, R₆, L₁, L₂, L₃ and L₄ are as defined under formula I above.

EMBODIMENT (A1)

Preferred are compounds of formula I-1, wherein
A is C—H or N;
$R_1$ is $C_1$-$C_4$alkyl, $C_3$-$C_6$cycloalkyl-$C_1$-$C_4$alkyl or $C_3$-$C_6$cycloalkyl; $R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;
X and $R_6$ are as defined under formula I above;
$L_1$, $L_2$, $L_3$ and $L_4$ are as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

EMBODIMENT (A2)

A further preferred group of compounds of formula I are represented by the compounds of formula I-2

(I-2)

wherein the substituents X, A, R₁, R₂, R₆, L₁, L₂, L₃ and L₄ are as defined under formula I above.
Preferred are compounds of formula I-2, wherein
A is C—H or N;
$R_1$ is $C_1$-$C_4$alkyl, $C_3$-$C_6$cycloalkyl-$C_1$-$C_4$alkyl or $C_3$-$C_6$cycloalkyl; $R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;
X and $R_6$ are as defined under formula I above;
$L_1$, $L_2$, $L_3$ and $L_4$ are as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

EMBODIMENT (A3)

Also preferred are compounds of formula I-3;

(I-3)

wherein the substituents X, A, R₁, R₂, L₁, L₂, L₃ and L₄ are as defined under formula I above.
Preferred are compounds of formula I-3, wherein
A is C—H or N;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;
X and $R_6$ are as defined under formula I above;
$L_1$, $L_2$, $L_3$ and $L_4$ are as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

EMBODIMENT (A4)

Further preferred are compounds of formula I-1a (I-1a)

wherein J is selected from the group J₁-J₂₇
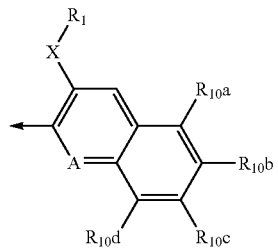
J₁
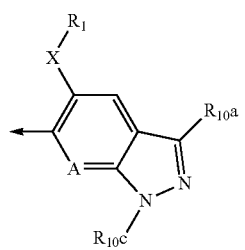
J₂
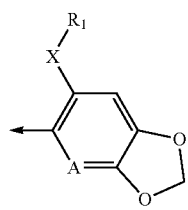
J₃
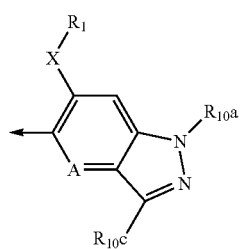
J₄
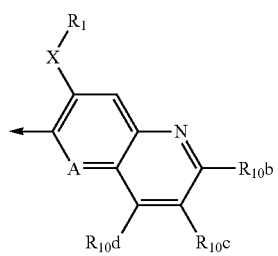
J₅
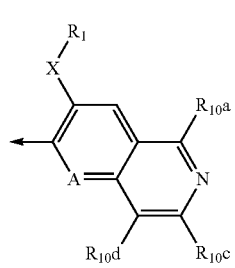
J₆
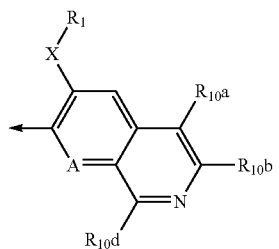
J₇
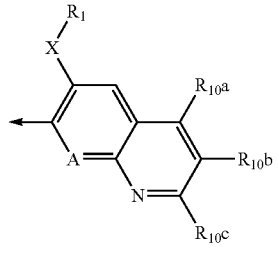
J₈
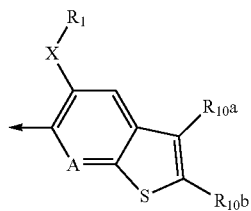
J₉
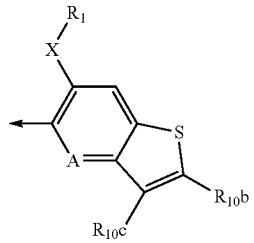
J₁₀
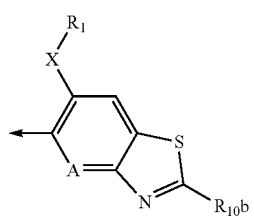
J₁₁
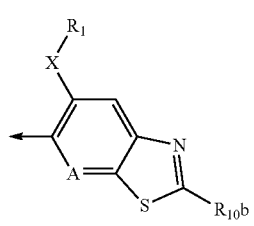
J₁₂

-continued
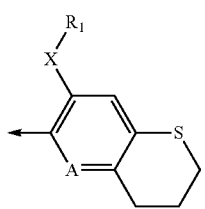
J13
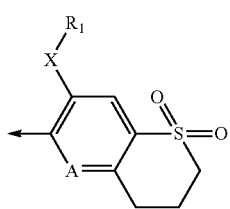
J14
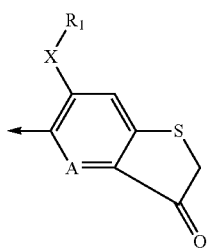
J15
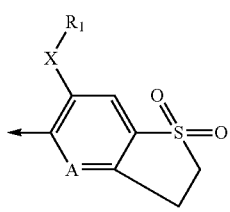
J16
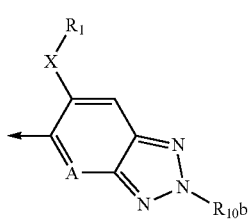
J17
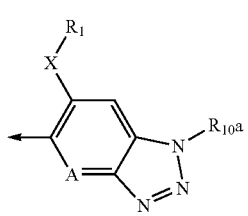
J18
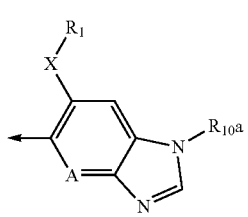
J19
-continued
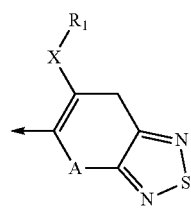
J20
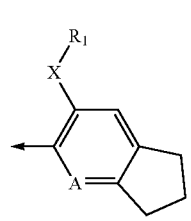
J21
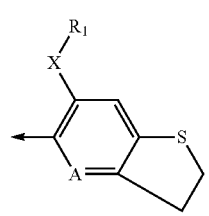
J22
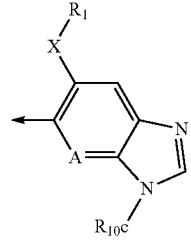
J23
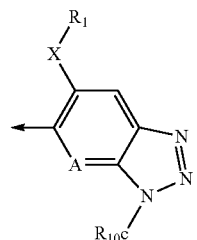
J24
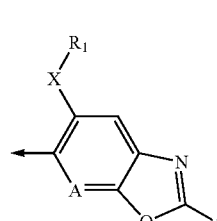
J25
and
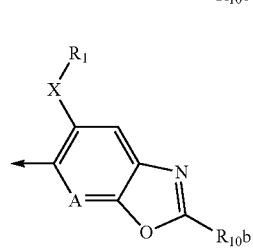
J26

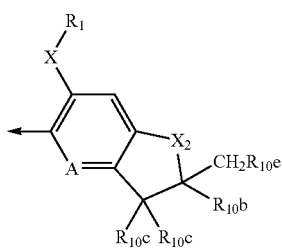
J27
preferably J₁ to J₂₆;
and A, R₁, R₂, X, R₁₀ₐ, R₁₀ᵦ, R₁₀c, R₁₀d, are as defined in embodiment (A1), X₂ is oxygen or S(O)n₁, wherein n₁ is 0, 1, or 2, and R₁₀ₑ is hydrogen, C₁-C₆alkyl, C₁-C₆haloalkyl, C₃-C₆cycloalkyl or and C₃-C₆halocycloalkyl.
EMBODIMENT (A5)
Further preferred are compounds of formula I-2a
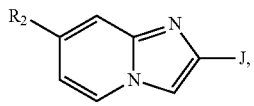
(I-2a)
wherein J is selected from the group J₁-J₂₇
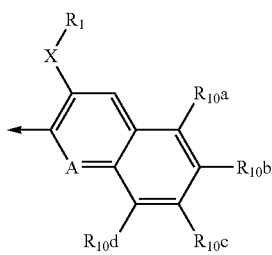
J₁
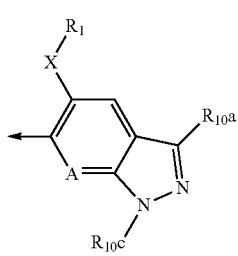
J₂
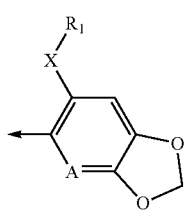
J₃
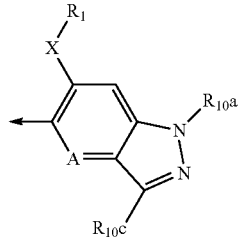
J₄
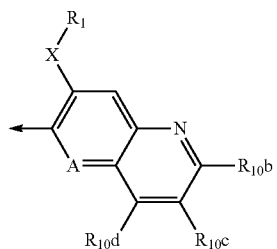
J₅
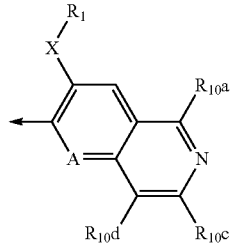
J₆
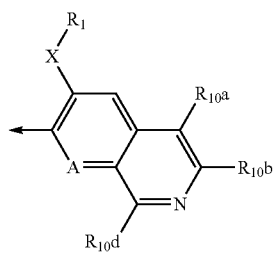
J₇
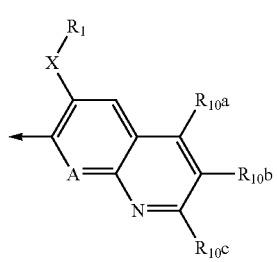
J₈
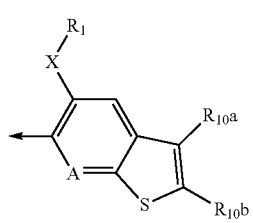
J₉

-continued
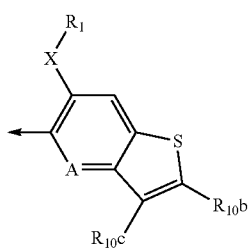
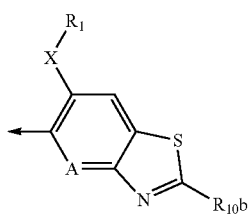
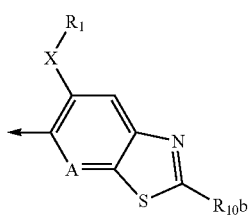
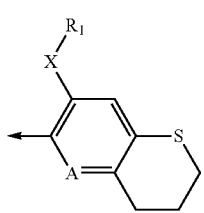
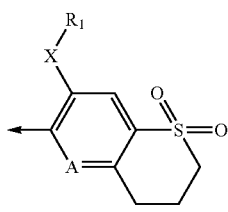
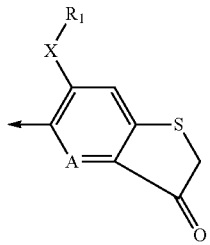
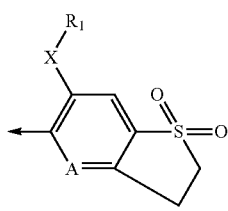
-continued
$J_{10}$
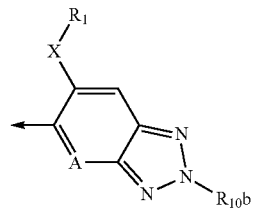
$J_{11}$
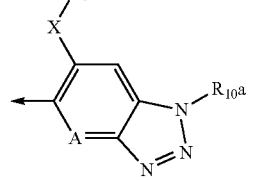
$J_{12}$
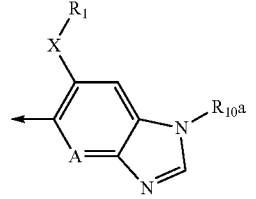
$J_{13}$
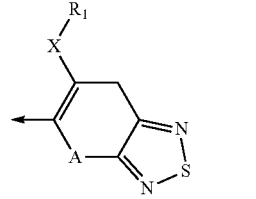
$J_{14}$
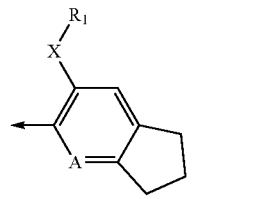
$J_{15}$
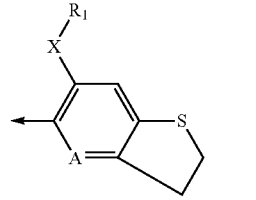
$J_{16}$
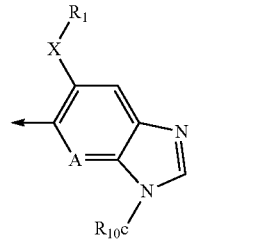
$J_{17}$
$J_{18}$
$J_{19}$
$J_{20}$
$J_{21}$
$J_{22}$
$J_{23}$

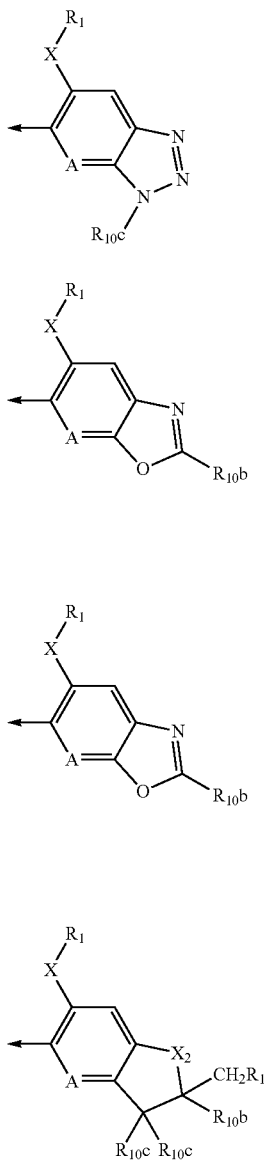
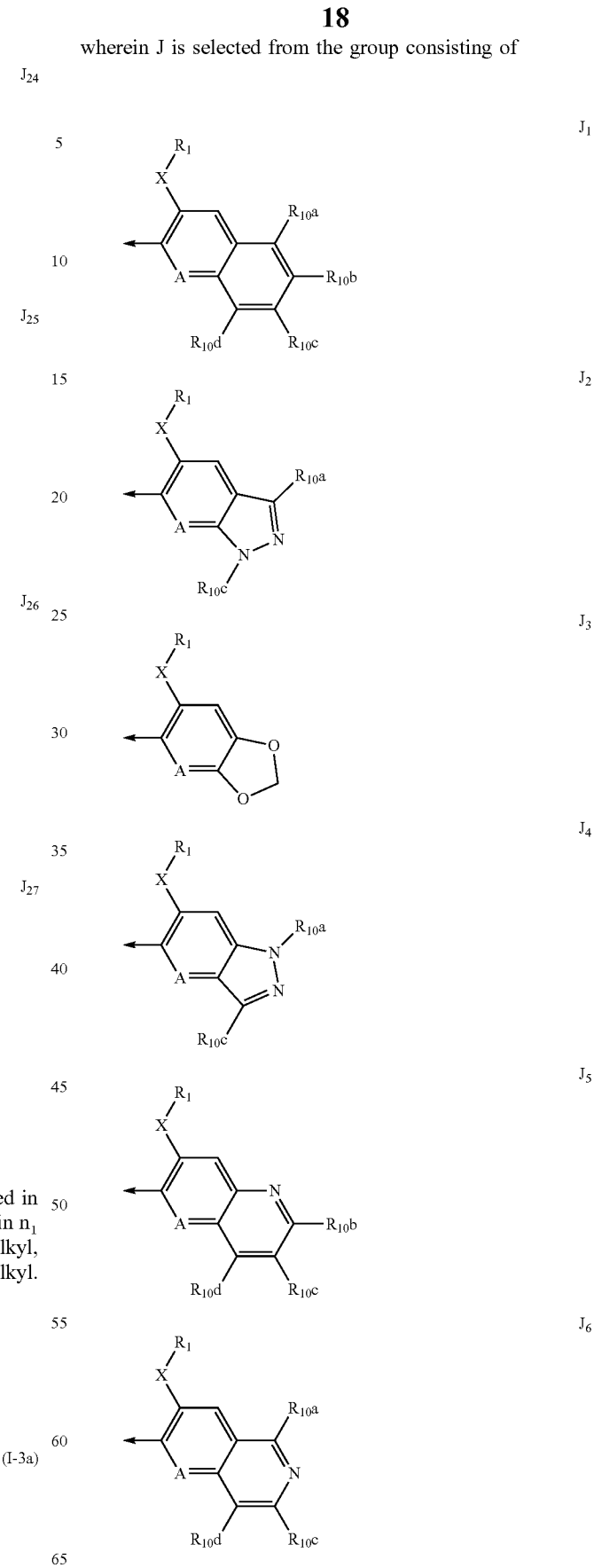
preferably J₁ to J₂₆;
and A, R₁, R₂, X, $R_{10a}$, $R_{10b}$, $R_{10c}$, $R_{10d}$, are as defined in embodiment (A2), and X₂ is oxygen or S(O)n₁ (wherein n₁ is 0, 1, or 2) and $R_{10e}$ is hydrogen, $C_1$-$C_6$alkyl, $C_1$-$C_6$haloalkyl, $C_3$-$C_6$cycloalkyl, and $C_3$-$C_6$halocycloalkyl.
EMBODIMENT (A6)
Further preferred are compounds of formula I-3a
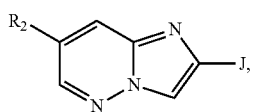
(I-3a)

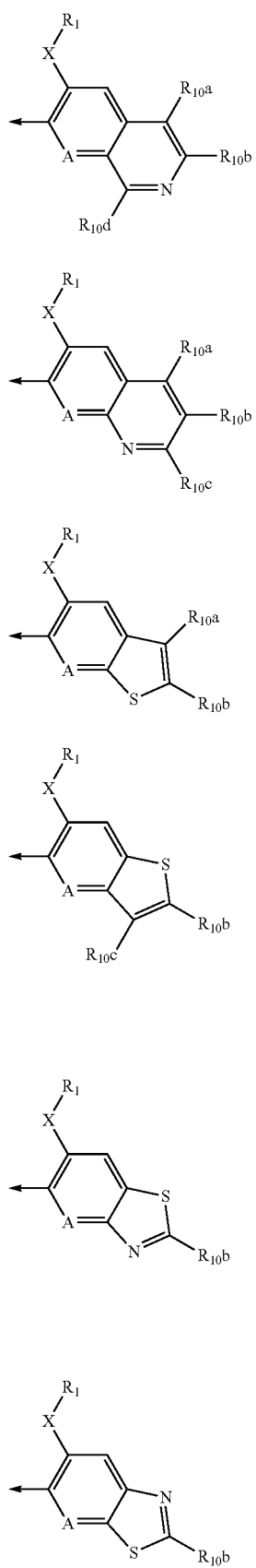
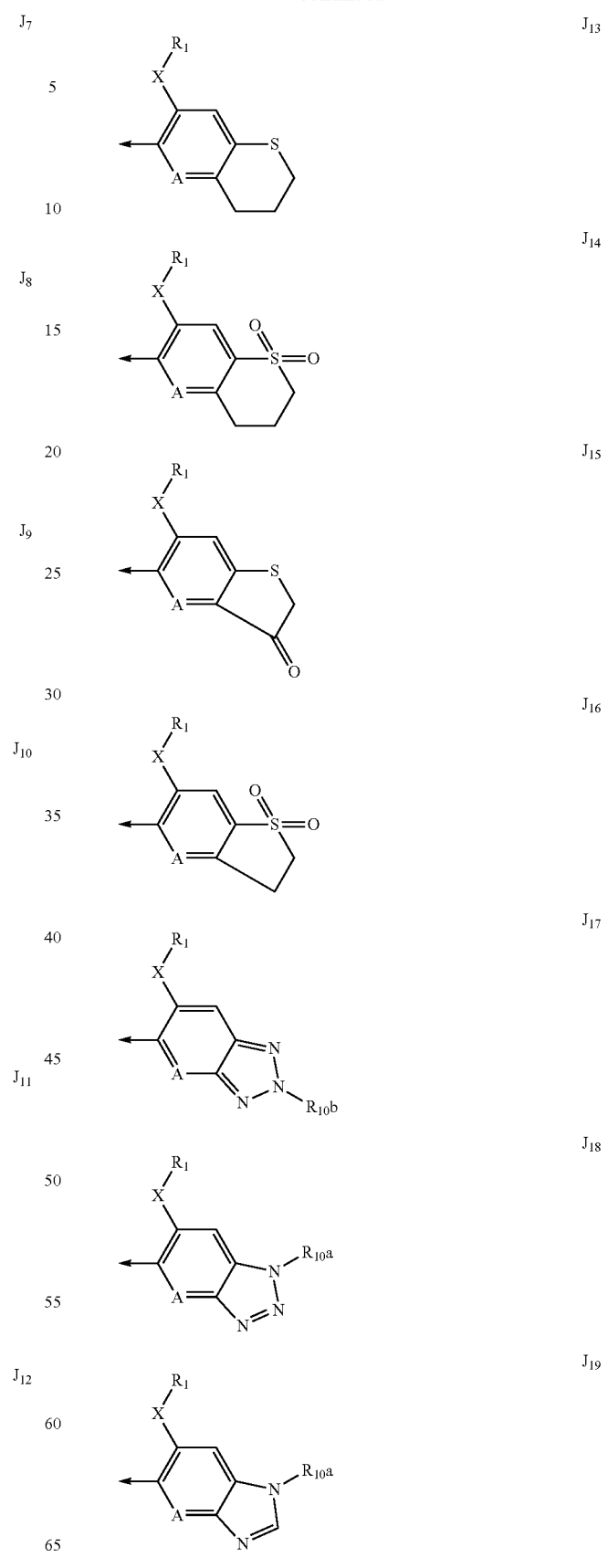

-continued

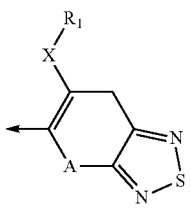
J20

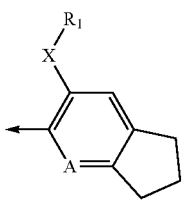
J21

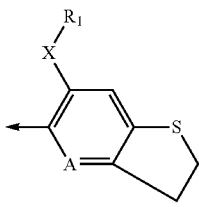
J22

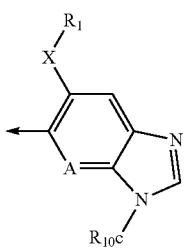
J23

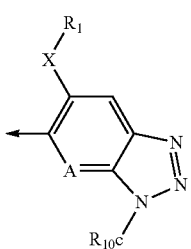
J24

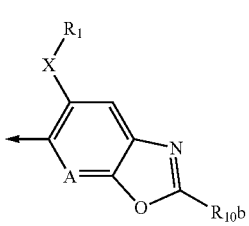
J25 and

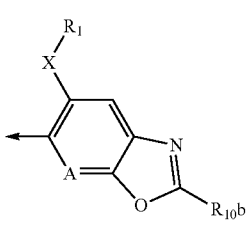
J26

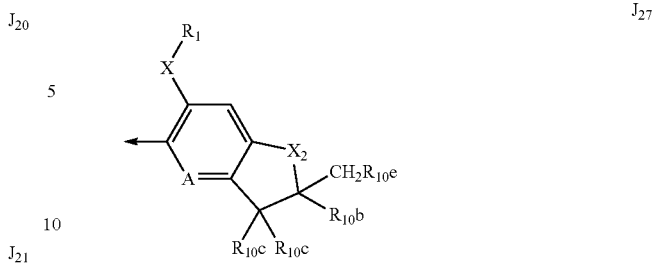
J27 preferably $J_1$ to $J_{26}$;

and A, $R_1$, $R_2$, X, $R_{10a}$, $R_{10b}$, $R_{10c}$, $R_{10d}$, are as defined in embodiment (A3), and $X_2$ is oxygen or $S(O)n_1$ (wherein $n_1$ is 0, 1, or 2) and $R_{10e}$ is hydrogen, $C_1$-$C_6$alkyl, $C_1$-$C_6$haloalkyl, $C_3$-$C_6$cycloalkyl, and $C_3$-$C_6$halocycloalkyl.

EMBODIMENT (A7)

Further preferred are compounds of formula I-1a

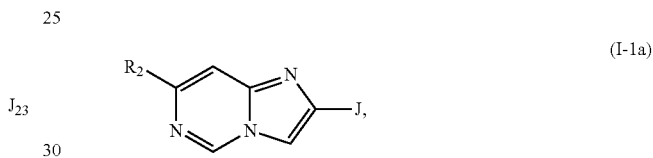
(I-1a)

wherein J is as defined under Embodiment (A4) above and

A is C—H or N;

$R_1$ is $C_1$-$C_4$ alkyl;

$R_2$ is —OCF$_3$, —SCF$_3$, —S(O)CF$_3$, —S(O)$_2$CF$_3$ or CF$_3$;

X is as defined under formula I above; and $R_{10a}$, $R_{10b}$, $R_{10c}$, and $R_{10d}$, independently from each other, are hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (A8)

Further preferred are compounds of formula I-2a

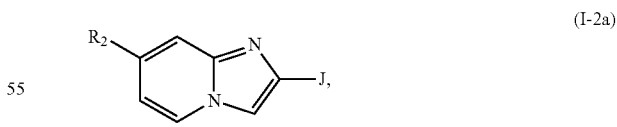
(I-2a)

wherein J is as defined under Embodiment (A5) above;

A is C—H or N;

$R_1$ is ethyl;

$R_2$ is CF$_3$;

$R_{10a}$, $R_{10b}$, $R_{10c}$, and $R_{10d}$, independently from each other, are hydrogen, Br, Cl, I, F, cyano, methyl, ethyl, isopropyl, propyl, trifluoromethyl, CF$_3$CH$_2$—, CH$_3$O, —SCF$_3$, —S(O)CF$_3$ or —S(O)$_2$CF$_3$.

EMBODIMENT (A9)

Further preferred are compounds of formula I-3a

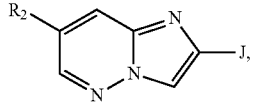
(I-3a)

wherein J is as defined under Embodiment (A6) above;
A is C—H or N;
$R_1$ is ethyl;
$R_2$ is $CF_3$;
X is as defined under formula I above; and
$R_{10a}$, $R_{10b}$, $R_{10c}$, and $R_{10d}$, independently from each other, are hydrogen, Br, Cl, I, F, cyano, methyl, or trifluoromethyl.

In all of the preferred embodiments A4-A9, J is preferably $J_1$, $J_2$, $J_3$, $J_4$, $J_5$, $J_6$, $J_{12}$, $J_{17}$, $J_{18}$, $J_{24}$, $J_{19}$, $J_{20}$ $J_{23}$, or $J_{27}$. In particular J is $J_1$, $J_{19}$ or $J_{27}$.

EMBODIMENT (A10)

Further preferred compounds of formula I are those, wherein
A is CH or N;
X is $SO_2$;
$R_1$ is $C_1$-$C_4$alkyl;
$R_2$ is $C_1$-$C_4$haloalkyl or $C_1$-$C_4$haloalkylsufanyl;
$G_1$ is N or $CR_4$; wherein $R_4$ is hydrogen;
$G_2$ is $CR_5$, wherein $R_5$ is hydrogen;
$R_6$ is hydrogen;
$L_1$, $L_2$, $L_3$ and $L_4$ form together with the two carbon atoms to which $L_1$ and $L_4$ are attached, a phenyl group or form an imidiazolyl group which can be mono- or di-substituted by substituents selected from the group consisting of $C_1$-$C_4$alkyl and $C_1$-$C_4$haloalkyl.

The process according to the invention for preparing compounds of formula (I) is carried out by methods known to those skilled in the art, or described for example in WO 2013/191113, WO 2009/131237, WO 2011/043404, WO 2011/040629, WO 2010/125985, WO 2012/086848, WO 2013/018928, WO 2013/180193 and WO 2013/180194, and involves reaction of a compound of formula II,

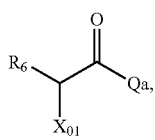
(II)

wherein $X_{01}$ is a halogen and $R_6$ is as described in formula I, and wherein Qa is the group

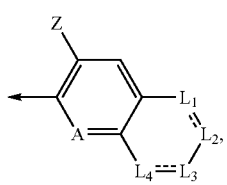
(Qa)

wherein Z is X—$R_1$ or a leaving group, for example a halogen, and wherein X, $R_1$, $L_1$, $L_2$, $L_3$, $L_4$ and A are as described under formula I above, and wherein the arrow in the radical Qa shows the point of attachment to the carbon atom of the carbonyl group in the compound of formula II, optionally in the presence of a suitable base in an inert solvent with a compound of formula III

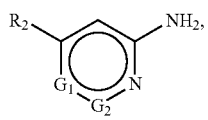
(III)

wherein $R_2$, $G_1$ and $G_2$ are as described in formula (I). Such reactions are well known in the literature and have been described for example in WO 2013/191113.

A further process to prepare compounds of formula I, involves reacting a compound of formula III with a compound of IIa

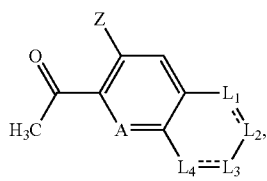
(IIa)

In the presence of a Lewis acid, such as Zinc(II)iodide or Indium(III)triflate, in an inert solvent such as chlorobenzene or 1,2, dichlorobenzene, with a catalytic amount of a copper (II) salt, such as Cu(II)acetate, under an oxygen or air atmosphere at temperatures between 100-180° C., preferably 110-140° C., to give compounds of formula I wherein $R_6$ is hydrogen. Such reactions have previously been described in the literature (see *Adv. Synth. Catal.* 2013, 355, 1741-1747, and *J. Org. Chem.*, 2013, 78, 12494-12504). Halogenation of compounds of formula I, wherein $R_6$ is hydrogen, with a halogenating agent such as N-chlorosuccinamide, N-bromosuccinamide, or N-iodosuccinamide, in a polar aprotic solvent such as acetonitrile or dimethylformamide, at ambient temperature, leads to compounds of formula $I_{a01}$

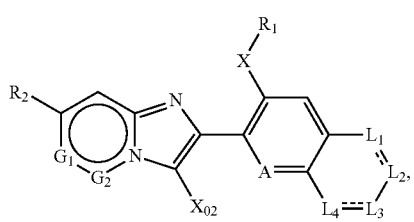
(Ia01)

wherein X, $G_1$, $G_2$, $R_1$, $R_2$, $L_1$, $L_2$, $L_3$, $L_4$ and A are as described in formula (I), and $X_{02}$ is halogen. Compounds of formula $I_{a01}$ can be reacted with compounds $R_6$-$M_0$, wherein $M_0$ is a boronic acid, in the presence of a palladium catalyst to give compounds of formula I. When $M_0$ is a boronic acid, the reaction is usually carried out in the presence of a base, for example potassium carbonate, cesium carbonate, or potassium phosphate, in an inert solvent, such as dioxane, optionally in the presence of water, with a palladium(0) catalyst, for example tetrakis(triphenylphosphine)palladium, at a temperature between 80-120° C. Such Suzuki reactions are well precedented in the literature, see for example Masuda, Naoyuki et al, WO 2012/133607.

Compounds of formula II and IIa can be prepared from compounds of formula IV,

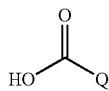

(IV)

Wherein Q is as described in formula I by, for example, the methods shown in scheme 1.

bromine and hydrobromic acid in acetic acid (as described in *Phosphorus, Sulfur and Silicon and the Related Elements*, 2013, 188(12), 1835-1844) or with, for example, copper(II) bromide in an inert solvent, for example chloroform, ethyl acetate and the like, as described in *J. Med. Chem.*, 2013, 56(1), 84-96. Alternatively compounds of formula II where $R_6$ is hydrogen, can be prepared directly from compounds of formula IVa by treatment with diazomethane or trimethyl silyl diazomethane and subsequent treatment with an halogen acid, for example, hydrobromic acid or hydrochloric acid in an inert solvent such as diethyl ether. Such procedures are well known in the literature, for example see *Eu. J. Med. Chem.*, 1987, 22(5), 457-62 and WO 2009010455.

Compounds of formula Ib,

Scheme 1

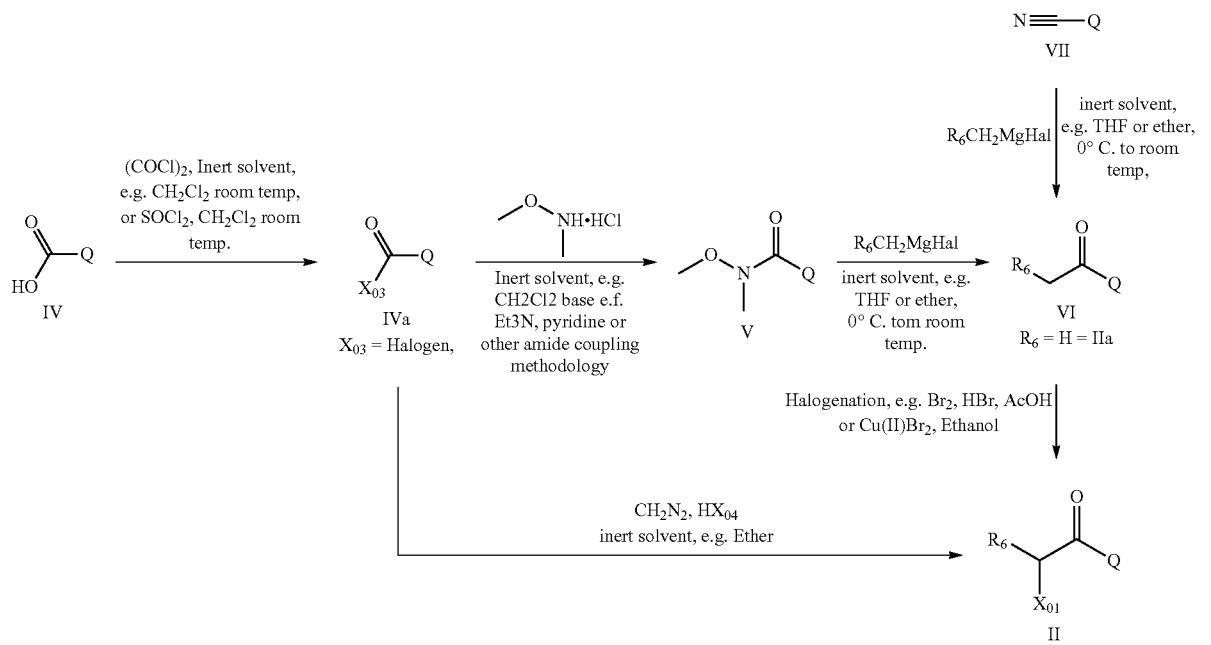

In scheme 1, an acyl halide of formula IVa is converted to a Weinreb amide V upon reaction with N,O-Dimethylhydroxylamine by methods known to those skilled in the art and described for example in C. Ferri, "*Reaktionen der Organischen Synthese*", Georg Thieme Verlag, Stuttgart, 1978, page 223ff. The amide of formula V is then reacted with a Grignard reagent of formula $R_6CH_2MgHal$ according to the method of Weinreb (*Tetrahedron Letters* 1981, 22, 3815-3818) to give compounds of formula VI and IIa (when $R_6$ is H). Compounds of formula VI and IIa can also be prepared by treatment of nitrile compounds of formula VII, wherein Q is as described in formula I, with a Grignard reagent of formula $R_6CH_2MgHal$, followed by acidic hydrolysis (as described in C. Ferri, "*Reaktionen der Organischen Synthese*", Georg Thieme Verlag, Stuttgart, 1978, page 223ff.).

Compounds of formula VI and IIa can be halogenated to compounds of formula II, with for example mixtures of

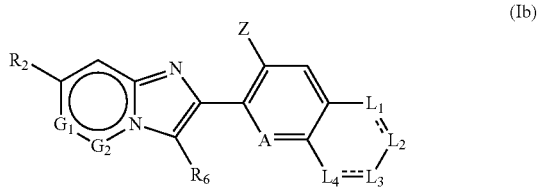

(Ib)

wherein Z is a leaving group, for example halogen, preferably fluorine or chlorine, and wherein $R_6$, $R_2$, $G_1$, $G_2$ A, $L_1$, $L_2$, $L_3$ and $L_4$ are as described under formula I above, can be reacted with compounds of formula VIII $R_1$—SH (VIII), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ic, wherein $R_1$ is as described under formula I above, and in which $R_6$, A, $R_2$, $L_1$, $L_2$, $L_3$, $L_4$, $G_1$ and $G_2$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO2013/018928. Examples of salts of the compound of formula VIII include compounds of the formula VIIIa $R_1$—S—M (VIIIa), wherein $R_1$ is as defined above and wherein M is, for example, sodium or potassium. This is illustrated for compounds of formula Ic in scheme 2:

ane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of of the sulfide compounds Ic to produce the sulfone compounds I (wherein X=$SO_2$). Such oxidation reactions are disclosed, for example, in WO 2013/018928.

Compounds of formula III

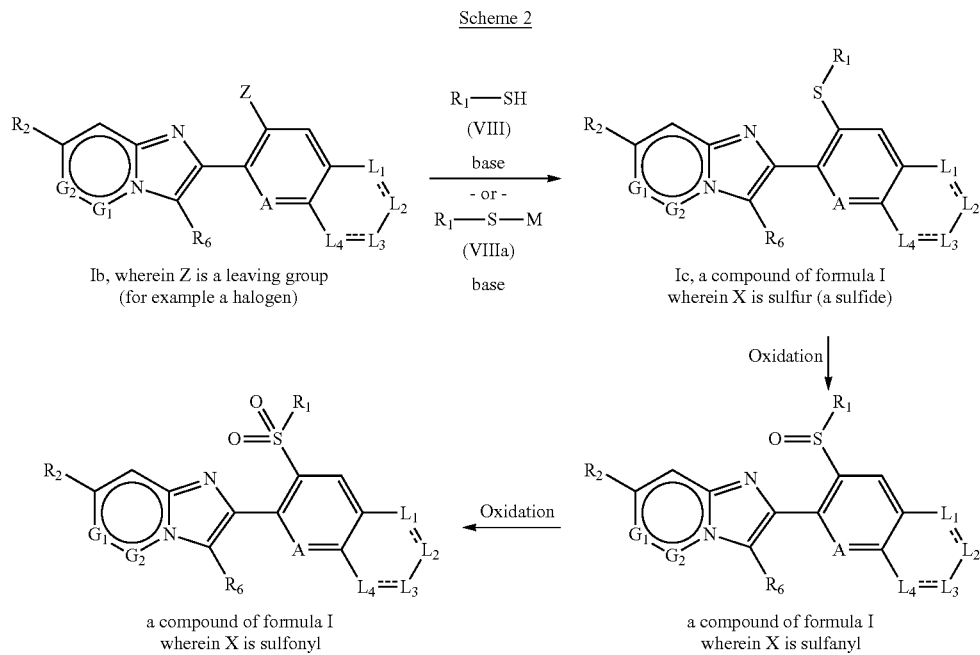

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al. in *Tetrahedron* 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ic above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane are either known, commercially available or may be made by methods known to a person skilled in the art. Examples of known compounds (CAS number) include, 4-Amino-6-bromopyrimidine ([1159818-57-1]), 4-Pyrimidinamine ([6-(trifluoromethyl)pyrimidin-4-amine ([1232134-17-6]), 6-aminopyrimidine-4-carbonitrile ([1353100-84-1]), 6-cyclopropylpyrimidin-4-amine ([7043-08-5]), 6-cyclobutylpyrimidin-4-amine ([1557338-24-5]), 4-(Difluoromethyl)pyridin-2-amine ([1346536-47-7]), 4-Bromopyridin-2-amine ([84249-14-9]), 2-Amino-4-(trifluoromethyl)pyridine ([106447-97-6]), 4-(1,1-difluoroethyl)pyridin-2-amine ([1522240-28-3]), 5-cyclopropylpyridazin-3-amine ([1619898-27-9]), 5-(trifluoromethyl)-3-Pyridazinamine ([1211591-88-6]), and 5-bromo-3-Pyridazinamine ([1187237-00-8]).

Compounds of formula IV,

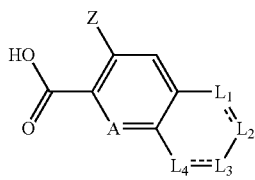

(IV)

wherein Z is X—$R_1$ or a leaving group or a group that could be transformed into a leaving group such as, for example halogen, amine or nitro, and wherein X, $R_1$, $L_1$, $L_2$, $L_3$, $L_4$ and A are as described under formula I above, are either known, commercially available or may be made by methods known to a person skilled in the art.

Compounds of formula IVb, wherein Q is as defined above, and wherein Z is a leaving group, for example halogen, preferably fluorine, chlorine, and wherein A, $L_1$, $L_2$, $L_3$ and $L_4$ are as described under formula I above, and wherein $R_{01}$ is $C_1$-$C_4$alkyl or hydrogen can be reacted with compounds of formula VIII $R_1$—SH    (VIII), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula IVc, wherein $R_{01}$ is $C_1$-$C_4$alkyl or hydrogen, $R_1$ is as described under formula I above, and in which A, $L_1$, $L_2$, $L_3$ and $L_4$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIII include compounds of the formula VIIIa;

$R_1$—S-M    (VIIIa), wherein $R_1$ is as defined above and wherein M is, for example, sodium or potassium. This is illustrated for compounds of formula IVc in scheme 3:

Scheme 3

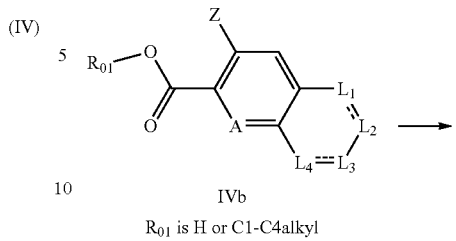

IVb $R_{01}$ is H or C1-C4alkyl

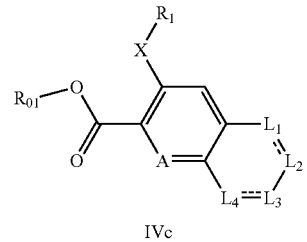

IVc

Alternatively, compounds of formula IVd, wherein $Z_1$ is $NH_2$ and wherein A, $L_1$, $L_2$, $L_3$ and $L_4$ are as described under formula I above, and wherein $R_{01}$ is $C_1$-$C_4$alkyl or hydrogen can be transformed to compounds of formula IVb via diazotation and reaction of the diazonium salt with a sulfide of formula $R_1$S—$SR_1$. This transformation can be carried out by methods known to a person skilled in the art and as described, for example in *Synthetic Communications*, 31(12), 1857-1861, 2001 or *Organic & Biomolecular Chemistry*, 6(4), 745-761, 2008. In an alternative synthesis, compounds of formula IVc, wherein $Z_1$ is $NH_2$ and wherein A, $L_1$, $L_2$, $L_3$ and $L_4$ are as described under formula I above, and wherein $R_{01}$ is $C_1$-$C_4$alkyl or hydrogen can be transformed to compounds of formula IVb via diazotation and reaction with sodium sulfide, followed by reduction of the disulfide with for example Zinc in acetic acid to give compounds of formula IVe This transformation has been described for example in US 20040116734 and *Chemische Berichte*, 120 (7), 1151-73, 1987. Alkylation of compound IVe with $R_1$—$X_{LG}$, wherein $R_1$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IVb, wherein $R_1$ is as described under formula I above (scheme 4)

Scheme 4

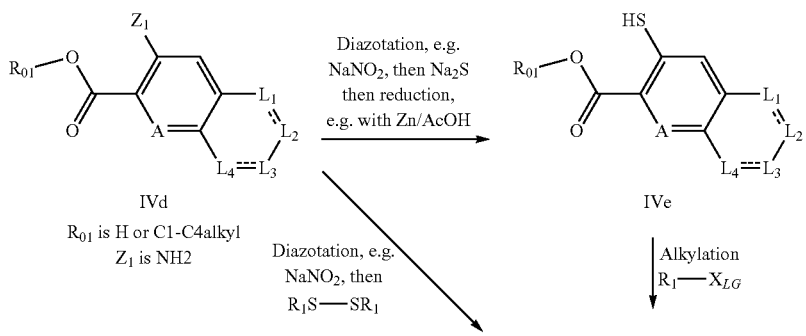

IVd
$R_{01}$ is H or C1-C4alkyl
$Z_1$ is NH2

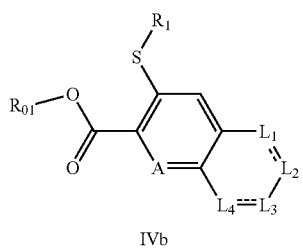

IVb

Compounds of formula IV may be obtained by reaction of a compound of formula IVb wherein $R_{01}$ is $C_1$-$C_4$alkyl via hydrolysis. For instance, in the case where $R_{01}$ is methyl or ethyl, the hydrolysis can be done with water and a base, such as potassium hydroxide or lithium hydroxide, in the absence or in the presence of a co-solvent, such as, tetrahydrofuran or methanol. In the case where $R_{01}$ is, for example, tert-butyl, the hydrolysis carried out in the presence of acid, such as trifluoroacetic acid, or hydrochloric acid. The reaction is carried out at a temperature of from −120° C. to +130° C., preferably from −100° C. to 100° C. (scheme 5)

Scheme 5

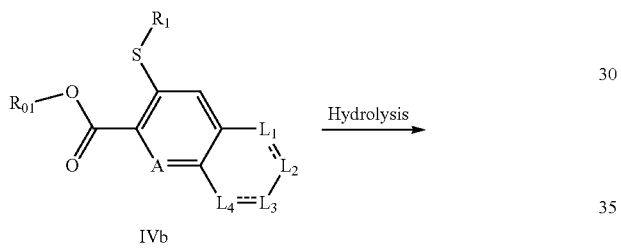

Alternatively, compound of formula IV may be prepared by reaction of a compound of formula VIIa wherein Z is a leaving group as nitro or halogen such as fluorine and wherein A, $L_1$, $L_2$, $L_3$ and $L_4$ are as described under formula I above by reaction of a compound of formula VIII or VIIIa $R_1$—SH (VIII), $R_1$—S-M (VIIIa), to give compounds of formula VIIb or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula VIIb, wherein $R_1$ is as described under formula I above, and in which A, $L_1$, $L_2$, $L_3$ and $L_4$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIII include compounds of the formula VIIIa $R_1$—S-M (VIIIa), wherein $R_1$ is as defined above and wherein M is, for example, sodium or potassium. Compounds of formula IV may be prepared by hydrolysis of the cyano of compound of formula VIIb in acidic or basic conditions. This transformation is well known and could be made by methods known to a person skilled in the art (see for example: *Comprehensive Organic Transformations: A Guide to Functional Group Preparations*. Edited by Richard C. Larock 1989, p 993, VCH publishers).

This is illustrated for compounds of formula II in scheme 6.

Scheme 6

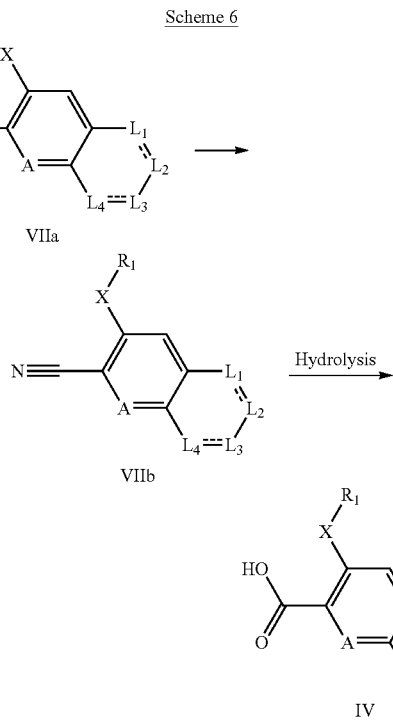

Compounds of formula VIIa are either known, commercially available or may be made by methods known to a person skilled in the art.

Alternatively, compound of formula IV may be prepared by reaction of a compound of formula IX where in Z is a leaving group such as nitro or halogen, such as fluorine, or a group X—$R_1$, and wherein A, $L_1$, $L_2$, $L_3$ and $L_4$ are as described under formula I above, by oxidation in presence of a oxidant such as oxygen, hydrogen peroxide or an metal oxide such as chromium trioxide, optionally in the presence of acid, such as sulfuric acid with or without metal catalyst. Such methyl oxidations to carboxylic acids are well known in the literature (see for example: *Comprehensive Organic Transformations: A Guide to Functional Group Preparations*. Edited by Richard C. Larock 1989 p 823, VCH publishers). This is illustrated for compounds of formula IV in scheme 7.

Scheme 7

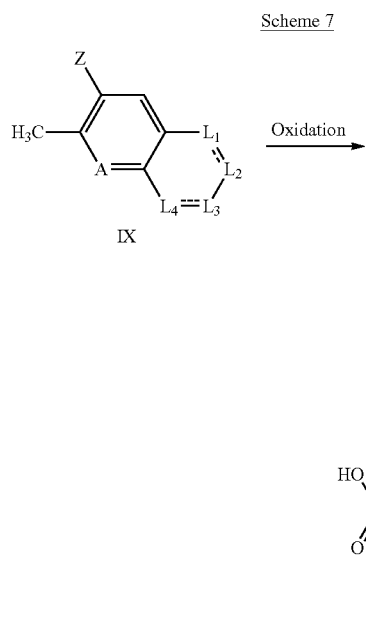

Compounds of formula IX are either known, commercially available or may be made by methods known to a person skilled in the art.

Compound of formula IIc, wherein R is $C_1$-$C_6$ Alkyl, A, $L_1$, $L_2$, $L_3$ and $L_4$ are as described under formula I above and Z is $NH_2$, may be prepared by reaction of a compound of formula (XIV) with a compound of formula XV wherein, for example $X_{00}$ is an halogen such as, for example, bromide and R is $C_1$-$C_6$ alkyl such as, for example, ethyl. these reactions are known to a person skilled in the art and are, for example described in *Tetrahedron*, 60 (2004) 2937-2942. This is illustrated for compounds of formula IIc in scheme 8.

Scheme 8

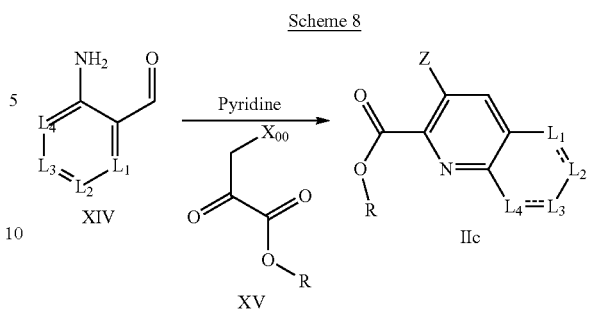

Alternatively, synthesis of compounds of formula I (benzimidazoles ($J_{19}$ and $J_{23}$) wherein: $L_1$=N or $NR_{10a}$, $L_2$=C—$R_{10b}$, $L_3$=N or N—$R_{10c}$, $L_4$=bond; benzothiadiazoles ($J_{20}$): $L_1$=N, $L_2$=S, $L_3$=N, $L_4$=bond; benzothiazoles ($J_{12}$): $L_1$=N, $L_2$=C—$R_{10b}$, $L_3$=S, $L_4$=bond; benzotriazoles ($J_{18}$, $J_{17}$ and $J_{24}$): $L_1$=N or N—$R_{10a}$, $L_2$=N or N—$R_{10b}$, $L_3$=N or N—$R_{10c}$, $L_4$=bond; benzoxazoles ($J_{25}$): $L_1$=N, $L_2$=C—$R_{10b}$, $L_3$=O, $L_4$=bond can be made via cyclisation of intermediates of formula XII or XIII as depicted in scheme 9. The synthesis of cyclic compounds as described in the Scheme 9 is well known and could be made by methods known to a person skilled in the art by analogy of what has described previously in literature. For example, for the synthesis of benzimidazoles starting from the intermediate type XIII (see *Monatshefte fuer Chemie* 2011, 142(1), 87-91 or *Organic Preparations and Procedures International*, 2013, 45(1), 57-65 or *Org. Prep. Proc. Int.* 2013, 45(2), 162-167 or *Tet. Lett.*, 2007 48(18), 3251-3254) or starting from the intermediate type XII, as for example in *J. Org. Chem.*, 2011, 76(23), 9577-9583 or *Tetrahedron* 2013, 69(6), 1717-1719. In general manner, see the review on the preparation of benzimidazoles in *The Chemistry of Heterocyclic Compounds*; Weissberger, A., Taylor, E. C., Eds. Wiley-VCH: New York, N.Y., 1981; Vol. 40, pp 6-60. For the synthesis of benzothiadiazoles starting from the intermediate of type XIII, see *Tetrahedron* 2005, 61(46), 10975-10982. For a more general review on the preparation and properties of benzimidazoles see; *Eur. J. Org. Chem.* 2013, 228-255. For the synthesis of benzotriazoles starting from the intermediate type XIII see for example *Bio. Med. Chem.*, 2010, 18(24), 8457-8462, using cyclocondensation chemistry as described in Scheme 9 (e.g. AcOH, $NaNO_2$). For a more general review on the preparation of benzotriazoles, see, for example, *J. Chem. Pharm. Res.*, 2011, 3(6), 375-381. For the synthesis of benzothiazoles starting from the intermediate type XII see for example, *J. Comb. Chem.*, 2009, 11(6), 1047-1049; *Chemistry—A European Journal*, 2012, 18(16), 4840-4843, or WO13066729. In addition, synthesis of benzothiazoles are well known and can be easily by methods known to those skilled in the art via other type of intermediates (see, for example, *J., Curr., Pharm., Res.*, 2010, 3(1), 13-23).

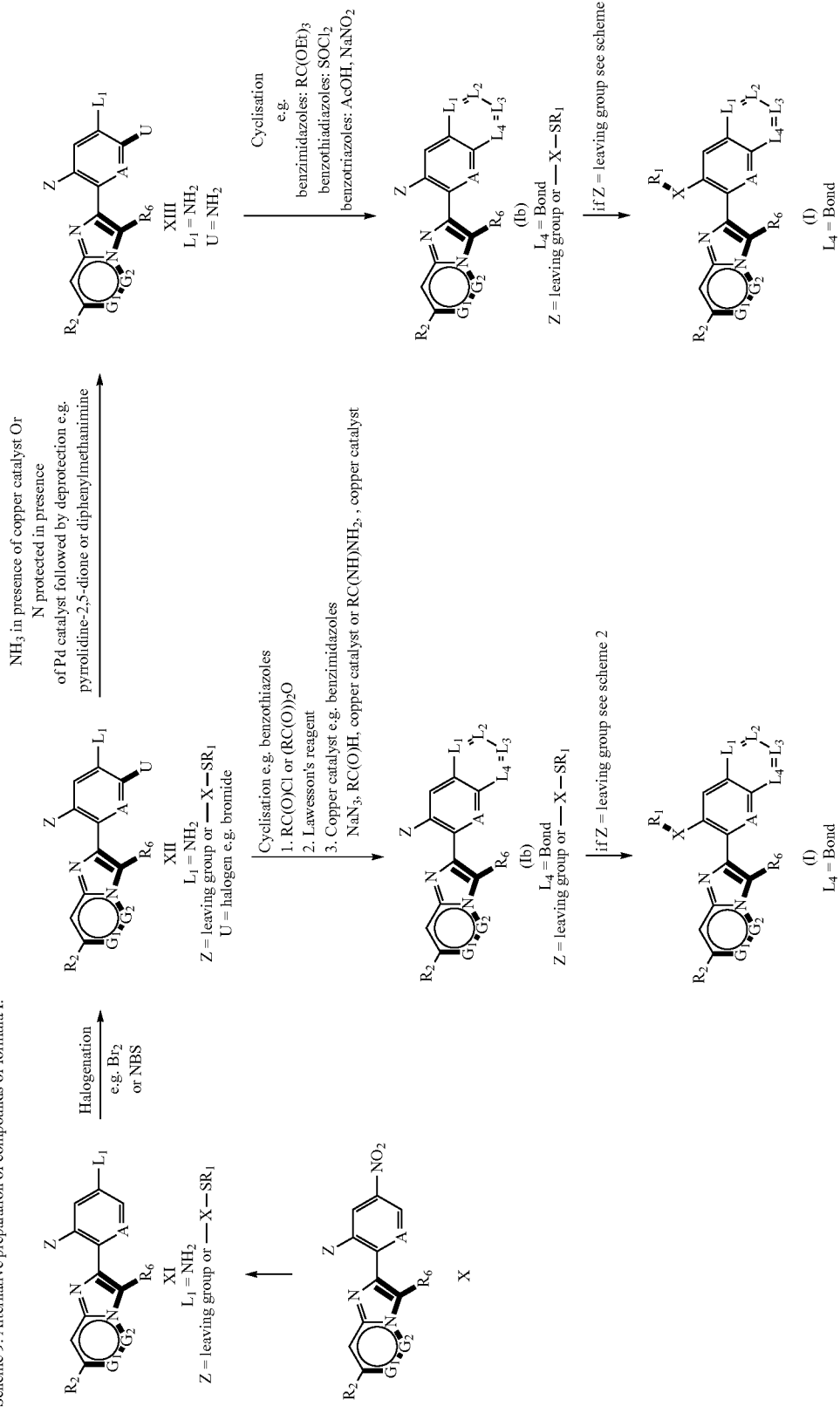

Compounds of formula X and XI may be prepared by in anology to reactions described in the literature (see JP 2014208695, WO 2014125651, WO 2014119670, WO 2014119679, WO 2014119674, WO 2014119494, WO 2014119699, WO 2014119672, JP 2014111558, and WO 2013018928. Compounds of formula Ib, and I containing an N—H as $L_1$, $L_2$ or $L_3$ can be reacted with an alkylating agent such as methyl iodide in presence of a base, such as potassium carbonate or sodium hydride, to give compounds of formula Ib, and I wherein $L_1$, $L_2$ or $L_3$ is an N—$CH_3$.

Compounds of formula IV, respectively IVe, IVf, IVg, and IVh, wherein L1 is oxygen, or $S(O)n_1$ (wherein $n_1$ is 0, 1, or 2), $R_{10a}$, $R_{10b}$, and $R_{10c}$ are as previously defined and $R_{10e}$ is hydrogen, $C_1$-$C_6$alkyl, $C_1$-$C_6$haloalkyl, $C_3$-$C_6$cycloalkyl, and $C_3$-$C_6$halocycloalkyl, $R_{10e}$ is $C_1$-$C_4C_6$alkyl, and Z is $X_1$—$R_1$, can be prepared as shown in Scheme 10:

Scheme 11

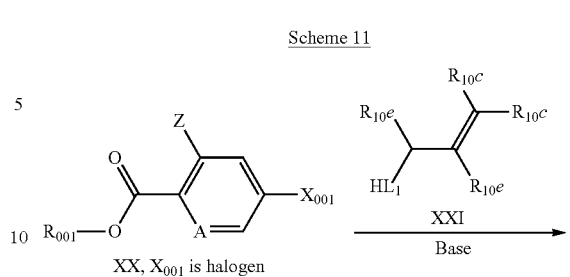

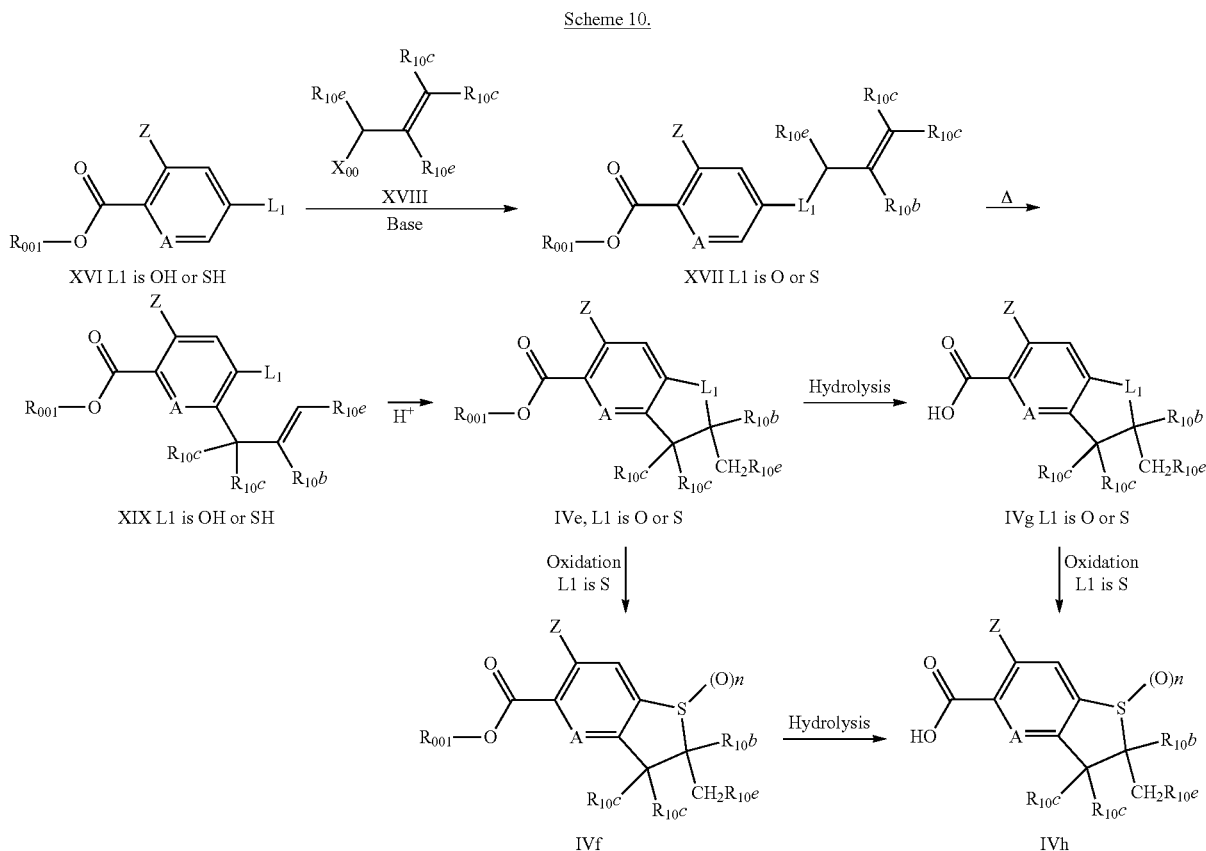

As shown in scheme 10, the synthesis requires:
1. Reacting compounds of formula XVI, wherein Z is $X_1$—$R_1$, with compounds of formula XVIII (wherein $X_{00}$ is a leaving group such as halogen, mesylate, or tosylate) in presence of a base such as, potassium carbonate in a solvent such as, acetone, acetonitrile or dimethylformamide or a mixture of solvent such as, dimethylformamide and acetone, optionally in the presence of a catalyst such as sodium iodine. The formation of the allyl ethers XVII is analogues to transformations well known to those skilled in the art, and analogus reactions have been described, for example in *Organic Letters*, 17(12), 3118-3121; 2015; *Tetrahedron*, 2004, 60, 7973-7981. Alternatively, compounds of formula XVII can be prepared as shown in scheme 11.

-continued

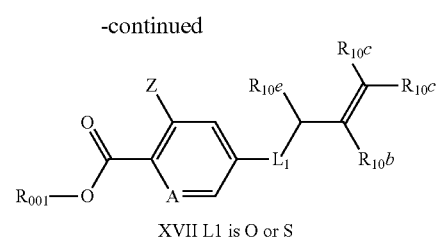

The reaction of a compound of formula XX, wherein $R_{001}$, Z and A are as previously described and $X_{001}$ is halogen, $R_{001}$ is $C_1$-$C_4$alkyl, Z is X—$R_1$, and A is as defined in formula 1 with a compound of formula XX1, wherein R10a, R10b, R10c, and R10e are as previously defined and L1 is sulfur or oxygen in the presence of a base, such as sodium hydride or cesium carbonate, in an insert solvent such as DMF leads to compounds of formula XVII.
2. A Claisen rearrangement of compounds of formula XVII under heating conditions to give compounds of formula XIX. This reaction and the conditions to realize it are well known to persons skilled in the art, see for example "*Strategic Applications of Named Reactions in Organic Synthesis*" by Kurti, Laszlo; Czako, Barbara; Editors; 2005, page 88.
3. Cyclising compounds of formula XIX under acidic conditions, for example organic acids such as acetuc of formic acid. Such transformations (intramolecular hydroalkoxylation) are well known to those skilled in the art and have been described, in for example, *Ang. Chem. Int. Ed.*, 54(13), 4014-4017, 2015 and cited references; *ChemCatChem*, 5(11), 3309-3315, 2013; *Chemistry—A European Journal*, 16(11), 3403-3422, 2010 references cited therein; *J. Org. Chem.*, 76(22), 9353-9361; 2011.

The compounds of formula IVe obtained can be hydrolysed to their corresponding acid IVg by methods known to those skilled in the art. Alternatively, the subgroup of compounds of formula IVf wherein L1 is SO (sulfoxide) and/or $SO_2$ (sulfone), may be obtained by means of an oxidation reaction of the corresponding sulfide compounds of formula IVe, wherein L1 is sulfur, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. Such oxidation reactions are disclosed, for example, in from Ger. Offen, DE 10130709, 2002 and PCT Int. App WO 9909023, 1999 Preparation of compounds of formula XX and XVI can be prepared by persons skilled in the art, by the use of protocols described previously in this patent, or with procedures described in WO 2015000715, US 20140018373 (WO 2012086848) or US 20140194290 (WO 2013018928).

For preparing all other compounds of the formula (I) functionalized according to the definitions of formula I, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 4 below can be prepared according to the methods described above. The examples which follow are intended to illustrate the invention and show preferred compounds of formula I. "Ph" represents the phenyl group.

TABLE 1

(I-1a)

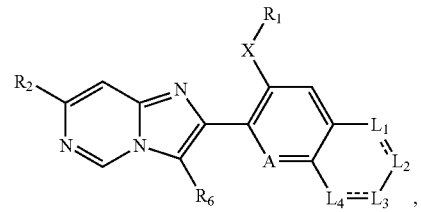

| Comp. No. | X | $R_1$ | A | $R_2$ | $R_6$ | $L_1$ | $L_2$ | $L_3$ | $L_4$ |
|---|---|---|---|---|---|---|---|---|---|
| 1.001 | S | $CH_2CH_3$ | C—H | $CF_3$ | H | CH | CH | CH | CH |
| 1.002 | SO | $CH_2CH_3$ | C—H | $CF_3$ | H | CH | CH | CH | CH |
| 1.003 | $SO_2$ | $CH_2CH_3$ | C—H | $CF_3$ | H | CH | CH | CH | CH |
| 1.004 | S | $CH_2CH_3$ | N | $CF_3$ | H | CH | CH | CH | CH |
| 1.005 | SO | $CH_2CH_3$ | N | $CF_3$ | H | CH | CH | CH | CH |
| 1.006 | $SO_2$ | $CH_2CH_3$ | N | $CF_3$ | H | CH | CH | CH | CH |
| 1.007 | S | $CH_2CH_3$ | C—H | $CF_3$ | H | O | $CH_2$ | O | bond |
| 1.008 | $SO_2$ | $CH_2CH_3$ | C—H | $CF_3$ | H | O | $CH_2$ | O | bond |
| 1.009 | S | $CH_2CH_3$ | C—H | $CF_3$ | H | CH | N | N—$CH_3$ | bond |
| 1.010 | SO | $CH_2CH_3$ | C—H | $CF_3$ | H | CH | N | N—$CH_3$ | bond |
| 1.011 | S | $CH_2CH_3$ | C—H | $CF_3$ | H | CH | N—$CH_3$ | N | bond |
| 1.012 | $SO_2$ | $CH_2CH_3$ | C—H | $CF_3$ | H | CH | N—$CH_3$ | N | bond |
| 1.013 | S | $CH_2CH_3$ | N | $CF_3$ | H | CH | N | N—$CH_3$ | bond |
| 1.014 | $SO_2$ | $CH_2CH_3$ | N | $CF_3$ | H | CH | N | N—$CH_3$ | bond |
| 1.015 | S | $CH_2CH_3$ | N | $CF_3$ | H | CH | N—$CH_3$ | N | bond |
| 1.016 | $SO_2$ | $CH_2CH_3$ | N | $CF_3$ | H | CH | N—$CH_3$ | N | bond |
| 1.017 | S | $CH_2CH_3$ | C—H | $CF_3$ | H | N | CH | CH | CH |
| 1.018 | $SO_2$ | $CH_2CH_3$ | C—H | $CF_3$ | H | N | CH | CH | CH |
| 1.019 | S | $CH_2CH_3$ | N | $CF_3$ | H | N | CH | CH | CH |
| 1.020 | $SO_2$ | $CH_2CH_3$ | N | $CF_3$ | H | N | CH | CH | CH |
| 1.021 | S | $CH_2CH_3$ | C—H | $CF_3$ | H | CH | N | CH | CH |
| 1.022 | $SO_2$ | $CH_2CH_3$ | C—H | $CF_3$ | H | CH | N | CH | CH |
| 1.023 | S | $CH_2CH_3$ | N | $CF_3$ | H | CH | N | CH | CH |
| 1.024 | $SO_2$ | $CH_2CH_3$ | N | $CF_3$ | H | CH | N | CH | CH |
| 1.025 | S | $CH_2CH_3$ | C—H | $CF_3$ | H | N—$CH_3$ | N | CH | bond |
| 1.026 | $SO_2$ | $CH_2CH_3$ | C—H | $CF_3$ | H | N—$CH_3$ | N | CH | bond |
| 1.027 | S | $CH_2CH_3$ | N | $CF_3$ | H | N—$CH_3$ | N | CH | bond |

TABLE 1-continued (I-1a)

| Comp. No. | X | R₁ | A | R₂ | R₆ | L₁ | L₂ | L₃ | L₄ |
|---|---|---|---|---|---|---|---|---|---|
| 1.028 | SO₂ | CH₂CH₃ | N | CF₃ | H | N—CH₃ | N | CH | bond |
| 1.029 | S | CH₂CH₃ | C—H | CF₃ | H | N | N—CH₃ | CH | bond |
| 1.030 | SO₂ | CH₂CH₃ | C—H | CF₃ | H | N | N—CH₃ | CH | bond |
| 1.031 | S | CH₂CH₃ | N | CF₃ | H | N | N—CH₃ | CH | bond |
| 1.032 | SO₂ | CH₂CH₃ | N | CF₃ | H | N | N—CH₃ | CH | bond |
| 1.033 | S | CH₂CH₃ | C—H | CF₃ | H | N | N—H | CH | bond |
| 1.034 | SO₂ | CH₂CH₃ | C—H | CF₃ | H | N | N—H | CH | bond |
| 1.035 | S | CH₂CH₃ | N | CF₃ | H | N | N—H | CH | bond |
| 1.036 | SO₂ | CH₂CH₃ | N | CF₃ | H | N | N—H | CH | bond |
| 1.037 | S | CH₂CH₃ | C—H | CF₃ | H | CH | N | N—H | bond |
| 1.038 | SO₂ | CH₂CH₃ | C—H | CF₃ | H | CH | N | N—H | bond |
| 1.039 | S | CH₂CH₃ | N | CF₃ | H | CH | N | N—H | bond |
| 1.040 | SO₂ | CH₂CH₃ | N | CF₃ | H | CH | N | N—H | bond |
| 1.041 | S | CH₂CH₃ | C—H | CF₃ | H | N | S | N | bond |
| 1.042 | SO₂ | CH₂CH₃ | C—H | CF₃ | H | N | S | N | bond |
| 1.043 | S | CH₂CH₃ | N | CF₃ | H | N | S | N | bond |
| 1.044 | SO₂ | CH₂CH₃ | N | CF₃ | H | N | S | N | bond |
| 1.045 | S | CH₂CH₃ | C—H | CF₃ | H | N | NH | N | bond |
| 1.046 | SO₂ | CH₂CH₃ | C—H | CF₃ | H | N | NH | N | bond |
| 1.047 | S | CH₂CH₃ | N | CF₃ | H | N | NH | N | bond |
| 1.048 | SO₂ | CH₂CH₃ | N | CF₃ | H | N | NH | N | bond |
| 1.049 | S | CH₂CH₃ | C—H | CF₃ | H | N | N—CH₃ | N | bond |
| 1.050 | SO₂ | CH₂CH₃ | C—H | CF₃ | H | N | N—CH₃ | N | bond |
| 1.051 | S | CH₂CH₃ | N | CF₃ | H | N | N—CH₃ | N | bond |
| 1.052 | SO₂ | CH₂CH₃ | N | CF₃ | H | N | N—CH₃ | N | bond |
| 1.053 | S | CH₂CH₃ | C—H | CF₃ | H | N | N | N—CH₃ | bond |
| 1.054 | SO₂ | CH₂CH₃ | C—H | CF₃ | H | N | N | N—CH₃ | bond |
| 1.055 | S | CH₂CH₃ | N | CF₃ | H | N | N | N—CH₃ | bond |
| 1.056 | SO₂ | CH₂CH₃ | N | CF₃ | H | N | N | N—CH₃ | bond |
| 1.057 | S | CH₂CH₃ | C—H | CF₃ | H | N—CH₃ | N | N | bond |
| 1.058 | SO₂ | CH₂CH₃ | C—H | CF₃ | H | N—CH₃ | N | N | bond |
| 1.059 | S | CH₂CH₃ | N | CF₃ | H | N—CH₃ | N | N | bond |
| 1.060 | SO₂ | CH₂CH₃ | N | CF₃ | H | N—CH₃ | N | N | bond |
| 1.061 | S | CH₂CH₃ | C—H | CF₃ | H | CH | C—CF₃ | CH | CH |
| 1.062 | SO₂ | CH₂CH₃ | C—H | CF₃ | H | CH | C—CF₃ | CH | CH |
| 1.063 | S | CH₂CH₃ | N | CF₃ | H | CH | C—CF₃ | CH | CH |
| 1.064 | SO₂ | CH₂CH₃ | N | CF₃ | H | CH | C—CF₃ | CH | CH |
| 1.065 | S | CH₂CH₃ | C—H | CF₃ | H | CH | C—F | CH | CH |
| 1.066 | SO₂ | CH₂CH₃ | C—H | CF₃ | H | CH | C—F | CH | CH |
| 1.067 | S | CH₂CH₃ | N | CF₃ | H | CH | C—F | CH | CH |
| 1.068 | SO₂ | CH₂CH₃ | N | CF₃ | H | CH | C—F | CH | CH |
| 1.069 | S | CH₂CH₃ | C—H | CF₃ | H | N | C—H | S | bond |
| 1.070 | SO₂ | CH₂CH₃ | C—H | CF₃ | H | N | C—H | S | bond |
| 1.071 | S | CH₂CH₃ | N | CF₃ | H | N | C—H | S | bond |
| 1.072 | SO₂ | CH₂CH₃ | N | CF₃ | H | N | C—H | S | bond |
| 1.073 | S | CH₂CH₃ | C—H | CF₃ | H | N | C—CH₃ | S | bond |
| 1.074 | SO₂ | CH₂CH₃ | C—H | CF₃ | H | N | C—CH₃ | S | bond |
| 1.075 | S | CH₂CH₃ | N | CF₃ | H | N | C—CH₃ | S | bond |
| 1.076 | SO₂ | CH₂CH₃ | N | CF₃ | H | N | C—CH₃ | S | bond |
| 1.077 | S | CH₂CH₃ | C—H | CF₃ | H | N | C—CF₃ | S | bond |
| 1.078 | SO₂ | CH₂CH₃ | C—H | CF₃ | H | N | C—CF₃ | S | bond |
| 1.079 | S | CH₂CH₃ | N | CF₃ | H | N | C—CF₃ | S | bond |
| 1.080 | SO₂ | CH₂CH₃ | N | CF₃ | H | N | C—CF₃ | S | bond |
| 1.081 | S | CH₂CH₃ | C—H | CF₃ | H | S | C—H | N | bond |
| 1.082 | SO₂ | CH₂CH₃ | C—H | CF₃ | H | S | C—H | N | bond |
| 1.083 | S | CH₂CH₃ | N | CF₃ | H | S | C—H | N | bond |
| 1.084 | SO₂ | CH₂CH₃ | N | CF₃ | H | S | C—H | N | bond |
| 1.085 | S | CH₂CH₃ | C—H | CF₃ | H | S | C—CH₃ | N | bond |
| 1.086 | SO₂ | CH₂CH₃ | C—H | CF₃ | H | S | C—CH₃ | N | bond |
| 1.087 | S | CH₂CH₃ | N | CF₃ | H | S | C—CH₃ | N | bond |
| 1.088 | SO₂ | CH₂CH₃ | N | CF₃ | H | S | C—CH₃ | N | bond |
| 1.089 | S | CH₂CH₃ | C—H | CF₃ | H | S | C—CF₃ | N | bond |
| 1.090 | SO₂ | CH₂CH₃ | C—H | CF₃ | H | S | C—CF₃ | N | bond |
| 1.091 | S | CH₂CH₃ | N | CF₃ | H | S | C—CF₃ | N | bond |
| 1.092 | SO₂ | CH₂CH₃ | N | CF₃ | H | S | C—CF₃ | N | bond |

TABLE 1-continued (I-1a)

[Structure of formula I-1a showing imidazo-fused ring system with substituents R1, R2, R6, X, A, L1, L2, L3, L4]

| Comp. No. | X | R₁ | A | R₂ | R₆ | L₁ | L₂ | L₃ | L₄ |
|---|---|---|---|---|---|---|---|---|---|
| 1.093 | S | CH₂CH₃ | C—H | CF₃ | H | N—H | C—CF₃ | N | bond |
| 1.094 | SO₂ | CH₂CH₃ | C—H | CF₃ | H | N—H | C—CF₃ | N | bond |
| 1.095 | S | CH₂CH₃ | N | CF₃ | H | N—H | C—CF₃ | N | bond |
| 1.096 | SO₂ | CH₂CH₃ | N | CF₃ | H | N—H | C—CF₃ | N | bond |
| 1.097 | S | CH₂CH₃ | C—H | CF₃ | H | N—H | C—CH₃ | N | bond |
| 1.098 | SO₂ | CH₂CH₃ | C—H | CF₃ | H | N—H | C—CH₃ | N | bond |
| 1.099 | S | CH₂CH₃ | N | CF₃ | H | N—H | C—CH₃ | N | bond |
| 1.100 | SO₂ | CH₂CH₃ | N | CF₃ | H | N—H | C—CH₃ | N | bond |
| 1.101 | S | CH₂CH₃ | C—H | CF₃ | H | N—H | CH | N | bond |
| 1.102 | SO₂ | CH₂CH₃ | C—H | CF₃ | H | N—H | CH | N | bond |
| 1.103 | S | CH₂CH₃ | N | CF₃ | H | N—H | CH | N | bond |
| 1.104 | SO₂ | CH₂CH₃ | N | CF₃ | H | N—H | CH | N | bond |
| 1.105 | S | CH₂CH₃ | C—H | CF₃ | H | N—CH₃ | CH | N | bond |
| 1.106 | SO₂ | CH₂CH₃ | C—H | CF₃ | H | N—CH₃ | CH | N | bond |
| 1.107 | S | CH₂CH₃ | N | CF₃ | H | N—CH₃ | CH | N | bond |
| 1.108 | SO₂ | CH₂CH₃ | N | CF₃ | H | N—CH₃ | CH | N | bond |
| 1.109 | S | CH₂CH₃ | C—H | CF₃ | H | N—CH₃ | C—CH₃ | N | bond |
| 1.110 | SO₂ | CH₂CH₃ | C—H | CF₃ | H | N—CH₃ | C—CH₃ | N | bond |
| 1.111 | S | CH₂CH₃ | N | CF₃ | H | N—CH₃ | C—CH₃ | N | bond |
| 1.112 | SO₂ | CH₂CH₃ | N | CF₃ | H | N—CH₃ | C—CH₃ | N | bond |
| 1.113 | S | CH₂CH₃ | C—H | CF₃ | H | N—CH₃ | C—CF₃ | N | bond |
| 1.114 | SO₂ | CH₂CH₃ | C—H | CF₃ | H | N—CH₃ | C—CF₃ | N | bond |
| 1.115 | S | CH₂CH₃ | N | CF₃ | H | N—CH₃ | C—CF₃ | N | bond |
| 1.116 | SO₂ | CH₂CH₃ | N | CF₃ | H | N—CH₃ | C—CF₃ | N | bond |
| 1.117 | S | CH₂CH₃ | C—H | CF₃ | H | N | CH | N—CH₃ | bond |
| 1.118 | SO₂ | CH₂CH₃ | C—H | CF₃ | H | N | CH | N—CH₃ | bond |
| 1.119 | S | CH₂CH₃ | N | CF₃ | H | N | CH | N—CH₃ | bond |
| 1.120 | SO₂ | CH₂CH₃ | N | CF₃ | H | N | CH | N—CH₃ | bond |
| 1.121 | S | CH₂CH₃ | C—H | CF₃ | H | N | C—CH₃ | N—CH₃ | bond |
| 1.122 | SO₂ | CH₂CH₃ | C—H | CF₃ | H | N | C—CH₃ | N—CH₃ | bond |
| 1.123 | S | CH₂CH₃ | N | CF₃ | H | N | C—CH₃ | N—CH₃ | bond |
| 1.124 | SO₂ | CH₂CH₃ | N | CF₃ | H | N | C—CH₃ | N—CH₃ | bond |
| 1.125 | S | CH₂CH₃ | C—H | CF₃ | H | N | C—CF₃ | N—CH₃ | bond |
| 1.126 | SO₂ | CH₂CH₃ | C—H | CF₃ | H | N | C—CF₃ | N—CH₃ | bond |
| 1.127 | S | CH₂CH₃ | N | CF₃ | H | N | C—CF₃ | N—CH₃ | bond |
| 1.128 | SO₂ | CH₂CH₃ | N | CF₃ | H | N | C—CF₃ | N—CH₃ | bond |
| 1.129 | S | CH₂CH₃ | C—H | SCF₃ | H | N—CH₃ | C—CF₃ | N | bond |
| 1.130 | SO₂ | CH₂CH₃ | C—H | SCF₃ | H | N—CH₃ | C—CF₃ | N | bond |

This table discloses the 128 compounds of the formula I-1a: and the N-oxides or tautomers of the compounds of Table 1.

TABLE 2

(I-1b)

[Structure of formula I-1b showing imidazo-fused ring system with substituents R1, R2, R6, X, A, L1, L2, L3, L4]

| Comp. No. | X | R₁ | A | R₂ | R₆ | L₁ | L₂ | L₃ | L₄ |
|---|---|---|---|---|---|---|---|---|---|
| 2.001 | S | CH₂CH₃ | C—H | CF₃ | H | CH | CH | CH | CH |
| 2.002 | SO | CH₂CH₃ | C—H | CF₃ | H | CH | CH | CH | CH |
| 2.003 | SO₂ | CH₂CH₃ | C—H | CF₃ | H | CH | CH | CH | CH |
| 2.004 | S | CH₂CH₃ | N | CF₃ | H | CH | CH | CH | CH |

TABLE 2-continued

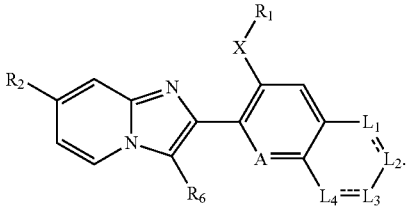

(I-1b)

| Comp. No. | X | R₁ | A | R₂ | R₆ | L₁ | L₂ | L₃ | L₄ |
|---|---|---|---|---|---|---|---|---|---|
| 2.005 | SO | CH₂CH₃ | N | CF₃ | H | CH | CH | CH | CH |
| 2.006 | SO₂ | CH₂CH₃ | N | CF₃ | H | CH | CH | CH | CH |
| 2.007 | S | CH₂CH₃ | C—H | CF₃ | H | O | CH₂ | O | bond |
| 2.008 | SO₂ | CH₂CH₃ | C—H | CF₃ | H | O | CH₂ | O | bond |
| 2.009 | S | CH₂CH₃ | C—H | CF₃ | H | CH | N | N—CH₃ | bond |
| 2.010 | SO₂ | CH₂CH₃ | C—H | CF₃ | H | CH | N | N—CH₃ | bond |
| 2.011 | S | CH₂CH₃ | C—H | CF₃ | H | CH | N—CH₃ | N | bond |
| 2.012 | SO₂ | CH₂CH₃ | C—H | CF₃ | H | CH | N—CH₃ | N | bond |
| 2.013 | S | CH₂CH₃ | N | CF₃ | H | CH | N | N—CH₃ | bond |
| 2.014 | SO₂ | CH₂CH₃ | N | CF₃ | H | CH | N | N—CH₃ | bond |
| 2.015 | S | CH₂CH₃ | N | CF₃ | H | CH | N—CH₃ | N | bond |
| 2.016 | SO₂ | CH₂CH₃ | N | CF₃ | H | CH | N—CH₃ | N | bond |
| 2.017 | S | CH₂CH₃ | C—H | CF₃ | H | N | CH | CH | CH |
| 2.018 | SO₂ | CH₂CH₃ | C—H | CF₃ | H | N | CH | CH | CH |
| 2.019 | S | CH₂CH₃ | N | CF₃ | H | N | CH | CH | CH |
| 2.020 | SO₂ | CH₂CH₃ | N | CF₃ | H | N | CH | CH | CH |
| 2.021 | S | CH₂CH₃ | C—H | CF₃ | H | CH | N | CH | CH |
| 2.022 | SO₂ | CH₂CH₃ | C—H | CF₃ | H | CH | N | CH | CH |
| 2.023 | S | CH₂CH₃ | N | CF₃ | H | CH | N | CH | CH |
| 2.024 | SO₂ | CH₂CH₃ | N | CF₃ | H | CH | N | CH | CH |
| 2.025 | S | CH₂CH₃ | C—H | CF₃ | H | N—CH₃ | N | CH | bond |
| 2.026 | SO₂ | CH₂CH₃ | C—H | CF₃ | H | N—CH₃ | N | CH | bond |
| 2.027 | S | CH₂CH₃ | N | CF₃ | H | N—CH₃ | N | CH | bond |
| 2.028 | SO₂ | CH₂CH₃ | N | CF₃ | H | N—CH₃ | N | CH | bond |
| 2.029 | S | CH₂CH₃ | C—H | CF₃ | H | N | N—CH₃ | CH | bond |
| 2.030 | SO₂ | CH₂CH₃ | C—H | CF₃ | H | N | N—CH₃ | CH | bond |
| 2.031 | S | CH₂CH₃ | N | CF₃ | H | N | N—CH₃ | CH | bond |
| 2.032 | SO₂ | CH₂CH₃ | N | CF₃ | H | N | N—CH₃ | CH | bond |
| 2.033 | S | CH₂CH₃ | C—H | CF₃ | H | N | N—H | CH | bond |
| 2.034 | SO₂ | CH₂CH₃ | C—H | CF₃ | H | N | N—H | CH | bond |
| 2.035 | S | CH₂CH₃ | N | CF₃ | H | N | N—H | CH | bond |
| 2.036 | SO₂ | CH₂CH₃ | N | CF₃ | H | N | N—H | CH | bond |
| 2.037 | S | CH₂CH₃ | C—H | CF₃ | H | CH | N | N—H | bond |
| 2.038 | SO₂ | CH₂CH₃ | C—H | CF₃ | H | CH | N | N—H | bond |
| 2.039 | S | CH₂CH₃ | N | CF₃ | H | CH | N | N—H | bond |
| 2.040 | SO₂ | CH₂CH₃ | N | CF₃ | H | CH | N | N—H | bond |
| 2.041 | S | CH₂CH₃ | C—H | CF₃ | H | N | S | N | bond |
| 2.042 | SO₂ | CH₂CH₃ | C—H | CF₃ | H | N | S | N | bond |
| 2.043 | S | CH₂CH₃ | N | CF₃ | H | N | S | N | bond |
| 2.044 | SO₂ | CH₂CH₃ | N | CF₃ | H | N | S | N | bond |
| 2.045 | S | CH₂CH₃ | C—H | CF₃ | H | N | NH | N | bond |
| 2.046 | SO₂ | CH₂CH₃ | C—H | CF₃ | H | N | NH | N | bond |
| 2.047 | S | CH₂CH₃ | N | CF₃ | H | N | NH | N | bond |
| 2.048 | SO₂ | CH₂CH₃ | N | CF₃ | H | N | NH | N | bond |
| 2.049 | S | CH₂CH₃ | C—H | CF₃ | H | N | N—CH₃ | N | bond |
| 2.050 | SO₂ | CH₂CH₃ | C—H | CF₃ | H | N | N—CH₃ | N | bond |
| 2.051 | S | CH₂CH₃ | N | CF₃ | H | N | N—CH₃ | N | bond |
| 2.052 | SO₂ | CH₂CH₃ | N | CF₃ | H | N | N—CH₃ | N | bond |
| 2.053 | S | CH₂CH₃ | C—H | CF₃ | H | N | N | N—CH₃ | bond |
| 2.054 | SO₂ | CH₂CH₃ | C—H | CF₃ | H | N | N | N—CH₃ | bond |
| 2.055 | S | CH₂CH₃ | N | CF₃ | H | N | N | N—CH₃ | bond |
| 2.056 | SO₂ | CH₂CH₃ | N | CF₃ | H | N | N | N—CH₃ | bond |
| 2.057 | S | CH₂CH₃ | C—H | CF₃ | H | N—CH₃ | N | N | bond |
| 2.058 | SO₂ | CH₂CH₃ | C—H | CF₃ | H | N—CH₃ | N | N | bond |
| 2.059 | S | CH₂CH₃ | N | CF₃ | H | N—CH₃ | N | N | bond |
| 2.060 | SO₂ | CH₂CH₃ | N | CF₃ | H | N—CH₃ | N | N | bond |
| 2.061 | S | CH₂CH₃ | C—H | CF₃ | H | CH | C—CF₃ | CH | CH |
| 2.062 | SO₂ | CH₂CH₃ | C—H | CF₃ | H | CH | C—CF₃ | CH | CH |
| 2.063 | S | CH₂CH₃ | N | CF₃ | H | CH | C—CF₃ | CH | CH |
| 2.064 | SO₂ | CH₂CH₃ | N | CF₃ | H | CH | C—CF₃ | CH | CH |
| 2.065 | S | CH₂CH₃ | C—H | CF₃ | H | CH | C—F | CH | CH |
| 2.066 | SO₂ | CH₂CH₃ | C—H | CF₃ | H | CH | C—F | CH | CH |
| 2.067 | S | CH₂CH₃ | N | CF₃ | H | CH | C—F | CH | CH |
| 2.068 | SO₂ | CH₂CH₃ | N | CF₃ | H | CH | C—F | CH | CH |
| 2.069 | S | CH₂CH₃ | C—H | CF₃ | H | N | C—H | S | bond |

TABLE 2-continued (I-1b)

| Comp. No. | X | R₁ | A | R₂ | R₆ | L₁ | L₂ | L₃ | L₄ |
|---|---|---|---|---|---|---|---|---|---|
| 2.070 | SO₂ | CH₂CH₃ | C—H | CF₃ | H | N | C—H | S | bond |
| 2.071 | S | CH₂CH₃ | N | CF₃ | H | N | C—H | S | bond |
| 2.072 | SO₂ | CH₂CH₃ | N | CF₃ | H | N | C—H | S | bond |
| 2.073 | S | CH₂CH₃ | C—H | CF₃ | H | N | C—CH₃ | S | bond |
| 2.074 | SO₂ | CH₂CH₃ | C—H | CF₃ | H | N | C—CH₃ | S | bond |
| 2.075 | S | CH₂CH₃ | N | CF₃ | H | N | C—CH₃ | S | bond |
| 2.076 | SO₂ | CH₂CH₃ | N | CF₃ | H | N | C—CH₃ | S | bond |
| 2.077 | S | CH₂CH₃ | C—H | CF₃ | H | N | C—CF₃ | S | bond |
| 2.078 | SO₂ | CH₂CH₃ | C—H | CF₃ | H | N | C—CF₃ | S | bond |
| 2.079 | S | CH₂CH₃ | N | CF₃ | H | N | C—CF₃ | S | bond |
| 2.080 | SO₂ | CH₂CH₃ | N | CF₃ | H | N | C—CF₃ | S | bond |
| 2.081 | S | CH₂CH₃ | C—H | CF₃ | H | S | C—H | N | bond |
| 2.082 | SO₂ | CH₂CH₃ | C—H | CF₃ | H | S | C—H | N | bond |
| 2.083 | S | CH₂CH₃ | N | CF₃ | H | S | C—H | N | bond |
| 2.084 | SO₂ | CH₂CH₃ | N | CF₃ | H | S | C—H | N | bond |
| 2.085 | S | CH₂CH₃ | C—H | CF₃ | H | S | C—CH₃ | N | bond |
| 2.086 | SO₂ | CH₂CH₃ | C—H | CF₃ | H | S | C—CH₃ | N | bond |
| 2.087 | S | CH₂CH₃ | N | CF₃ | H | S | C—CH₃ | N | bond |
| 2.088 | SO₂ | CH₂CH₃ | N | CF₃ | H | S | C—CH₃ | N | bond |
| 2.089 | S | CH₂CH₃ | C—H | CF₃ | H | S | C—CF₃ | N | bond |
| 2.090 | SO₂ | CH₂CH₃ | C—H | CF₃ | H | S | C—CF₃ | N | bond |
| 2.091 | S | CH₂CH₃ | N | CF₃ | H | S | C—CF₃ | N | bond |
| 2.092 | SO₂ | CH₂CH₃ | N | CF₃ | H | S | C—CF₃ | N | bond |
| 2.093 | S | CH₂CH₃ | C—H | CF₃ | H | N—H | C—CF₃ | N | bond |
| 2.094 | SO₂ | CH₂CH₃ | C—H | CF₃ | H | N—H | C—CF₃ | N | bond |
| 2.095 | S | CH₂CH₃ | N | CF₃ | H | N—H | C—CF₃ | N | bond |
| 2.096 | SO₂ | CH₂CH₃ | N | CF₃ | H | N—H | C—CF₃ | N | bond |
| 2.097 | S | CH₂CH₃ | C—H | CF₃ | H | N—H | C—CH₃ | N | bond |
| 2.098 | SO₂ | CH₂CH₃ | C—H | CF₃ | H | N—H | C—CH₃ | N | bond |
| 2.099 | S | CH₂CH₃ | N | CF₃ | H | N—H | C—CH₃ | N | bond |
| 2.100 | SO₂ | CH₂CH₃ | N | CF₃ | H | N—H | C—CH₃ | N | bond |
| 2.101 | S | CH₂CH₃ | C—H | CF₃ | H | N—H | CH | N | bond |
| 2.102 | SO₂ | CH₂CH₃ | C—H | CF₃ | H | N—H | CH | N | bond |
| 2.103 | S | CH₂CH₃ | N | CF₃ | H | N—H | CH | N | bond |
| 2.104 | SO₂ | CH₂CH₃ | N | CF₃ | H | N—H | CH | N | bond |
| 2.105 | S | CH₂CH₃ | C—H | CF₃ | H | N—CH₃ | CH | N | bond |
| 2.106 | SO₂ | CH₂CH₃ | C—H | CF₃ | H | N—CH₃ | CH | N | bond |
| 2.107 | S | CH₂CH₃ | N | CF₃ | H | N—CH₃ | CH | N | bond |
| 2.108 | SO₂ | CH₂CH₃ | N | CF₃ | H | N—CH₃ | CH | N | bond |
| 2.109 | S | CH₂CH₃ | C—H | CF₃ | H | N—CH₃ | C—CH₃ | N | bond |
| 2.110 | SO₂ | CH₂CH₃ | C—H | CF₃ | H | N—CH₃ | C—CH₃ | N | bond |
| 2.111 | S | CH₂CH₃ | N | CF₃ | H | N—CH₃ | C—CH₃ | N | bond |
| 2.112 | SO₂ | CH₂CH₃ | N | CF₃ | H | N—CH₃ | C—CH₃ | N | bond |
| 2.113 | S | CH₂CH₃ | C—H | CF₃ | H | N—CH₃ | C—CF₃ | N | bond |
| 2.114 | SO₂ | CH₂CH₃ | C—H | CF₃ | H | N—CH₃ | C—CF₃ | N | bond |
| 2.115 | S | CH₂CH₃ | N | CF₃ | H | N—CH₃ | C—CF₃ | N | bond |
| 2.116 | SO₂ | CH₂CH₃ | N | CF₃ | H | N—CH₃ | C—CF₃ | N | bond |
| 2.117 | S | CH₂CH₃ | C—H | CF₃ | H | N | CH | N—CH₃ | bond |
| 2.118 | SO₂ | CH₂CH₃ | C—H | CF₃ | H | N | CH | N—CH₃ | bond |
| 2.119 | S | CH₂CH₃ | N | CF₃ | H | N | CH | N—CH₃ | bond |
| 2.120 | SO₂ | CH₂CH₃ | N | CF₃ | H | N | CH | N—CH₃ | bond |
| 2.121 | S | CH₂CH₃ | C—H | CF₃ | H | N | C—CH₃ | N—CH₃ | bond |
| 2.122 | SO₂ | CH₂CH₃ | C—H | CF₃ | H | N | C—CH₃ | N—CH₃ | bond |
| 2.123 | S | CH₂CH₃ | N | CF₃ | H | N | C—CH₃ | N—CH₃ | bond |
| 2.124 | SO₂ | CH₂CH₃ | N | CF₃ | H | N | C—CH₃ | N—CH₃ | bond |
| 2.125 | S | CH₂CH₃ | C—H | CF₃ | H | N | C—CF₃ | N—CH₃ | bond |
| 2.126 | SO₂ | CH₂CH₃ | C—H | CF₃ | H | N | C—CF₃ | N—CH₃ | bond |
| 2.127 | S | CH₂CH₃ | N | CF₃ | H | N | C—CF₃ | N—CH₃ | bond |
| 2.128 | SO₂ | CH₂CH₃ | N | CF₃ | H | N | C—CF₃ | N—CH₃ | bond |
| 2.129 | S | CH₂CH₃ | C—H | SCF₃ | H | N—CH₃ | C—CF₃ | N | bond |
| 2.130 | SO₂ | CH₂CH₃ | C—H | SCF₃ | H | N—CH₃ | C—CF₃ | N | bond |

This table discloses the 128 compounds of the formula I-1b:
and the N-oxides and tautomers of the compounds of Table 2.

TABLE 3

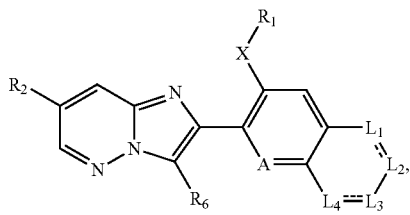

(I-1c)

| Comp. No. | X | R₁ | A | R₂ | R₆ | L₁ | L₂ | L₃ | L₄ |
|---|---|---|---|---|---|---|---|---|---|
| 3.001 | S | CH₂CH₃ | C—H | CF₃ | H | CH | CH | CH | CH |
| 3.002 | SO | CH₂CH₃ | C—H | CF₃ | H | CH | CH | CH | CH |
| 3.003 | SO₂ | CH₂CH₃ | C—H | CF₃ | H | CH | CH | CH | CH |
| 3.004 | S | CH₂CH₃ | N | CF₃ | H | CH | CH | CH | CH |
| 3.005 | SO | CH₂CH₃ | N | CF₃ | H | CH | CH | CH | CH |
| 3.006 | SO₂ | CH₂CH₃ | N | CF₃ | H | CH | CH | CH | CH |
| 3.007 | S | CH₂CH₃ | C—H | CF₃ | H | O | CH₂ | O | bond |
| 3.008 | SO₂ | CH₂CH₃ | C—H | CF₃ | H | O | CH₂ | O | bond |
| 3.009 | S | CH₂CH₃ | C—H | CF₃ | H | CH | N | N—CH₃ | bond |
| 3.010 | SO₂ | CH₂CH₃ | C—H | CF₃ | H | CH | N | N—CH₃ | bond |
| 3.011 | S | CH₂CH₃ | C—H | CF₃ | H | CH | N—CH₃ | N | bond |
| 3.012 | SO₂ | CH₂CH₃ | C—H | CF₃ | H | CH | N—CH₃ | N | bond |
| 3.013 | S | CH₂CH₃ | N | CF₃ | H | CH | N | N—CH₃ | bond |
| 3.014 | SO₂ | CH₂CH₃ | N | CF₃ | H | CH | N | N—CH₃ | bond |
| 3.015 | S | CH₂CH₃ | N | CF₃ | H | CH | N—CH₃ | N | bond |
| 3.016 | SO₂ | CH₂CH₃ | N | CF₃ | H | CH | N—CH₃ | N | bond |
| 3.017 | S | CH₂CH₃ | C—H | CF₃ | H | N | CH | CH | CH |
| 3.018 | SO₂ | CH₂CH₃ | C—H | CF₃ | H | N | CH | CH | CH |
| 3.019 | S | CH₂CH₃ | N | CF₃ | H | N | CH | CH | CH |
| 3.020 | SO₂ | CH₂CH₃ | N | CF₃ | H | N | CH | CH | CH |
| 3.021 | S | CH₂CH₃ | C—H | CF₃ | H | CH | N | CH | CH |
| 3.022 | SO₂ | CH₂CH₃ | C—H | CF₃ | H | CH | N | CH | CH |
| 3.023 | S | CH₂CH₃ | N | CF₃ | H | CH | N | CH | CH |
| 3.024 | SO₂ | CH₂CH₃ | N | CF₃ | H | CH | N | CH | CH |
| 3.025 | S | CH₂CH₃ | C—H | CF₃ | H | N—CH₃ | N | CH | bond |
| 3.026 | SO₂ | CH₂CH₃ | C—H | CF₃ | H | N—CH₃ | N | CH | bond |
| 3.027 | S | CH₂CH₃ | N | CF₃ | H | N—CH₃ | N | CH | bond |
| 3.028 | SO₂ | CH₂CH₃ | N | CF₃ | H | N—CH₃ | N | CH | bond |
| 3.029 | S | CH₂CH₃ | C—H | CF₃ | H | N | N—CH₃ | CH | bond |
| 3.030 | SO₂ | CH₂CH₃ | C—H | CF₃ | H | N | N—CH₃ | CH | bond |
| 3.031 | S | CH₂CH₃ | N | CF₃ | H | N | N—CH₃ | CH | bond |
| 3.032 | SO₂ | CH₂CH₃ | N | CF₃ | H | N | N—CH₃ | CH | bond |
| 3.033 | S | CH₂CH₃ | C—H | CF₃ | H | N | N—H | CH | bond |
| 3.034 | SO₂ | CH₂CH₃ | C—H | CF₃ | H | N | N—H | CH | bond |
| 3.035 | S | CH₂CH₃ | N | CF₃ | H | N | N—H | CH | bond |
| 3.036 | SO₂ | CH₂CH₃ | N | CF₃ | H | N | N—H | CH | bond |
| 3.037 | S | CH₂CH₃ | C—H | CF₃ | H | CH | N | N—H | bond |
| 3.038 | SO₂ | CH₂CH₃ | C—H | CF₃ | H | CH | N | N—H | bond |
| 3.039 | S | CH₂CH₃ | N | CF₃ | H | CH | N | N—H | bond |
| 3.040 | SO₂ | CH₂CH₃ | N | CF₃ | H | CH | N | N—H | bond |
| 3.041 | S | CH₂CH₃ | C—H | CF₃ | H | N | S | N | bond |
| 3.042 | SO₂ | CH₂CH₃ | C—H | CF₃ | H | N | S | N | bond |
| 3.043 | S | CH₂CH₃ | N | CF₃ | H | N | S | N | bond |
| 3.044 | SO₂ | CH₂CH₃ | N | CF₃ | H | N | S | N | bond |
| 3.045 | S | CH₂CH₃ | C—H | CF₃ | H | N | NH | N | bond |
| 3.046 | SO₂ | CH₂CH₃ | C—H | CF₃ | H | N | NH | N | bond |
| 3.047 | S | CH₂CH₃ | N | CF₃ | H | N | NH | N | bond |
| 3.048 | SO₂ | CH₂CH₃ | N | CF₃ | H | N | NH | N | bond |
| 3.049 | S | CH₂CH₃ | C—H | CF₃ | H | N | N—CH₃ | N | bond |
| 3.050 | SO₂ | CH₂CH₃ | C—H | CF₃ | H | N | N—CH₃ | N | bond |
| 3.051 | S | CH₂CH₃ | N | CF₃ | H | N | N—CH₃ | N | bond |
| 3.052 | SO₂ | CH₂CH₃ | N | CF₃ | H | N | N—CH₃ | N | bond |
| 3.053 | S | CH₂CH₃ | C—H | CF₃ | H | N | N | N—CH₃ | bond |
| 3.054 | SO₂ | CH₂CH₃ | C—H | CF₃ | H | N | N | N—CH₃ | bond |
| 3.055 | S | CH₂CH₃ | N | CF₃ | H | N | N | N—CH₃ | bond |
| 3.056 | SO₂ | CH₂CH₃ | N | CF₃ | H | N | N | N—CH₃ | bond |
| 3.057 | S | CH₂CH₃ | C—H | CF₃ | H | N—CH₃ | N | N | bond |
| 3.058 | SO₂ | CH₂CH₃ | C—H | CF₃ | H | N—CH₃ | N | N | bond |
| 3.059 | S | CH₂CH₃ | N | CF₃ | H | N—CH₃ | N | N | bond |
| 3.060 | SO₂ | CH₂CH₃ | N | CF₃ | H | N—CH₃ | N | N | bond |
| 3.061 | S | CH₂CH₃ | C—H | CF₃ | H | CH | C—CF₃ | CH | CH |

TABLE 3-continued

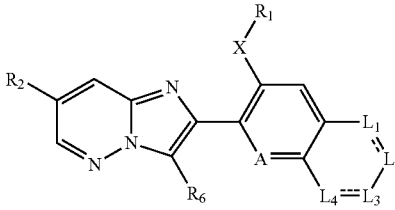

(I-1c)

| Comp. No. | X | R₁ | A | R₂ | R₆ | L₁ | L₂ | L₃ | L₄ |
|---|---|---|---|---|---|---|---|---|---|
| 3.062 | SO₂ | CH₂CH₃ | C—H | CF₃ | H | CH | C—CF₃ | CH | CH |
| 3.063 | S | CH₂CH₃ | N | CF₃ | H | CH | C—CF₃ | CH | CH |
| 3.064 | SO₂ | CH₂CH₃ | N | CF₃ | H | CH | C—CF₃ | CH | CH |
| 3.065 | S | CH₂CH₃ | C—H | CF₃ | H | CH | C—F | CH | CH |
| 3.066 | SO₂ | CH₂CH₃ | C—H | CF₃ | H | CH | C—F | CH | CH |
| 3.067 | S | CH₂CH₃ | N | CF₃ | H | CH | C—F | CH | CH |
| 3.068 | SO₂ | CH₂CH₃ | N | CF₃ | H | CH | C—F | CH | CH |
| 3.069 | S | CH₂CH₃ | C—H | CF₃ | H | N | C—H | S | bond |
| 3.070 | SO₂ | CH₂CH₃ | C—H | CF₃ | H | N | C—H | S | bond |
| 3.071 | S | CH₂CH₃ | N | CF₃ | H | N | C—H | S | bond |
| 3.072 | SO₂ | CH₂CH₃ | N | CF₃ | H | N | C—H | S | bond |
| 3.073 | S | CH₂CH₃ | C—H | CF₃ | H | N | C—CH₃ | S | bond |
| 3.074 | SO₂ | CH₂CH₃ | C—H | CF₃ | H | N | C—CH₃ | S | bond |
| 3.075 | S | CH₂CH₃ | N | CF₃ | H | N | C—CH₃ | S | bond |
| 3.076 | SO₂ | CH₂CH₃ | N | CF₃ | H | N | C—CH₃ | S | bond |
| 3.077 | S | CH₂CH₃ | C—H | CF₃ | H | N | C—CF₃ | S | bond |
| 3.078 | SO₂ | CH₂CH₃ | C—H | CF₃ | H | N | C—CF₃ | S | bond |
| 3.079 | S | CH₂CH₃ | N | CF₃ | H | N | C—CF₃ | S | bond |
| 3.080 | SO₂ | CH₂CH₃ | N | CF₃ | H | N | C—CF₃ | S | bond |
| 3.081 | S | CH₂CH₃ | C—H | CF₃ | H | S | C—H | N | bond |
| 3.082 | SO₂ | CH₂CH₃ | C—H | CF₃ | H | S | C—H | N | bond |
| 3.083 | S | CH₂CH₃ | N | CF₃ | H | S | C—H | N | bond |
| 3.084 | SO₂ | CH₂CH₃ | N | CF₃ | H | S | C—H | N | bond |
| 3.085 | S | CH₂CH₃ | C—H | CF₃ | H | S | C—CH₃ | N | bond |
| 3.086 | SO₂ | CH₂CH₃ | C—H | CF₃ | H | S | C—CH₃ | N | bond |
| 3.087 | S | CH₂CH₃ | N | CF₃ | H | S | C—CH₃ | N | bond |
| 3.088 | SO₂ | CH₂CH₃ | N | CF₃ | H | S | C—CH₃ | N | bond |
| 3.089 | S | CH₂CH₃ | C—H | CF₃ | H | S | C—CF₃ | N | bond |
| 3.090 | SO₂ | CH₂CH₃ | C—H | CF₃ | H | S | C—CF₃ | N | bond |
| 3.091 | S | CH₂CH₃ | N | CF₃ | H | S | C—CF₃ | N | bond |
| 3.092 | SO₂ | CH₂CH₃ | N | CF₃ | H | S | C—CF₃ | N | bond |
| 3.093 | S | CH₂CH₃ | C—H | CF₃ | H | N—H | C—CF₃ | N | bond |
| 3.094 | SO₂ | CH₂CH₃ | C—H | CF₃ | H | N—H | C—CF₃ | N | bond |
| 3.095 | S | CH₂CH₃ | N | CF₃ | H | N—H | C—CF₃ | N | bond |
| 3.096 | SO₂ | CH₂CH₃ | N | CF₃ | H | N—H | C—CF₃ | N | bond |
| 3.097 | S | CH₂CH₃ | C—H | CF₃ | H | N—H | C—CH₃ | N | bond |
| 3.098 | SO₂ | CH₂CH₃ | C—H | CF₃ | H | N—H | C—CH₃ | N | bond |
| 3.099 | S | CH₂CH₃ | N | CF₃ | H | N—H | C—CH₃ | N | bond |
| 3.100 | SO₂ | CH₂CH₃ | N | CF₃ | H | N—H | C—CH₃ | N | bond |
| 3.101 | S | CH₂CH₃ | C—H | CF₃ | H | N—H | CH | N | bond |
| 3.102 | SO₂ | CH₂CH₃ | C—H | CF₃ | H | N—H | CH | N | bond |
| 3.103 | S | CH₂CH₃ | N | CF₃ | H | N—H | CH | N | bond |
| 3.104 | SO₂ | CH₂CH₃ | N | CF₃ | H | N—H | CH | N | bond |
| 3.105 | S | CH₂CH₃ | C—H | CF₃ | H | N—CH₃ | CH | N | bond |
| 3.106 | SO₂ | CH₂CH₃ | C—H | CF₃ | H | N—CH₃ | CH | N | bond |
| 3.107 | S | CH₂CH₃ | N | CF₃ | H | N—CH₃ | CH | N | bond |
| 3.108 | SO₂ | CH₂CH₃ | N | CF₃ | H | N—CH₃ | CH | N | bond |
| 3.109 | S | CH₂CH₃ | C—H | CF₃ | H | N—CH₃ | C—CH₃ | N | bond |
| 3.110 | SO₂ | CH₂CH₃ | C—H | CF₃ | H | N—CH₃ | C—CH₃ | N | bond |
| 3.111 | S | CH₂CH₃ | N | CF₃ | H | N—CH₃ | C—CH₃ | N | bond |
| 3.112 | SO₂ | CH₂CH₃ | N | CF₃ | H | N—CH₃ | C—CH₃ | N | bond |
| 3.113 | S | CH₂CH₃ | C—H | CF₃ | H | N—CH₃ | C—CF₃ | N | bond |
| 3.114 | SO₂ | CH₂CH₃ | C—H | CF₃ | H | N—CH₃ | C—CF₃ | N | bond |
| 3.115 | S | CH₂CH₃ | N | CF₃ | H | N—CH₃ | C—CF₃ | N | bond |
| 3.116 | SO₂ | CH₂CH₃ | N | CF₃ | H | N—CH₃ | C—CF₃ | N | bond |
| 3.117 | S | CH₂CH₃ | C—H | CF₃ | H | N | CH | N—CH₃ | bond |
| 3.118 | SO₂ | CH₂CH₃ | C—H | CF₃ | H | N | CH | N—CH₃ | bond |
| 3.119 | S | CH₂CH₃ | N | CF₃ | H | N | CH | N—CH₃ | bond |
| 3.120 | SO₂ | CH₂CH₃ | N | CF₃ | H | N | CH | N—CH₃ | bond |
| 3.121 | S | CH₂CH₃ | C—H | CF₃ | H | N | C—CH₃ | N—CH₃ | bond |
| 3.122 | SO₂ | CH₂CH₃ | C—H | CF₃ | H | N | C—CH₃ | N—CH₃ | bond |
| 3.123 | S | CH₂CH₃ | N | CF₃ | H | N | C—CH₃ | N—CH₃ | bond |
| 3.124 | SO₂ | CH₂CH₃ | N | CF₃ | H | N | C—CH₃ | N—CH₃ | bond |
| 3.125 | S | CH₂CH₃ | C—H | CF₃ | H | N | C—CF₃ | N—CH₃ | bond |
| 3.126 | SO₂ | CH₂CH₃ | C—H | CF₃ | H | N | C—CF₃ | N—CH₃ | bond |

TABLE 3-continued

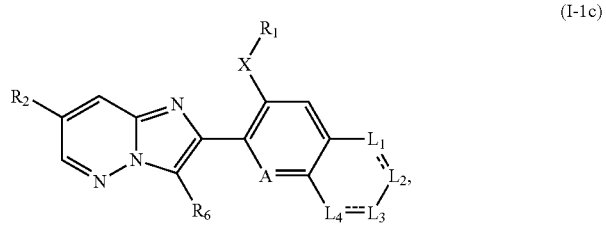

(I-1c)

| Comp. No. | X | $R_1$ | A | $R_2$ | $R_6$ | $L_1$ | $L_2$ | $L_3$ | $L_4$ |
|---|---|---|---|---|---|---|---|---|---|
| 3.127 | S | $CH_2CH_3$ | N | $CF_3$ | H | N | $C-CF_3$ | $N-CH_3$ | bond |
| 3.128 | $SO_2$ | $CH_2CH_3$ | N | $CF_3$ | H | N | $C-CF_3$ | $N-CH_3$ | bond |
| 3.129 | S | $CH_2CH_3$ | C—H | $SCF_3$ | H | $N-CH_3$ | $C-CF_3$ | N | bond |
| 3.130 | $SO_2$ | $CH_2CH_3$ | C—H | $SCF_3$ | H | $N-CH_3$ | $C-CF_3$ | N | bond |

This table discloses the 128 compounds of the formula I-1c: and the N-oxides and tautomers of the compounds of Table 3.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:
from the order Acarina, for example,
*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;
from the order Diptera, for example,
*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;
from the order Hemiptera, for example,
*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp, *Piezodorus* spp, *Rhodnius* spp., *Sahlbergella singularis, Scaptocoris castanea, Scotinophara* spp., *Thyanta* spp, *Triatoma* spp., *Vatiga illudens;*
*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii Scop., Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolo-*

*phium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., Diprionidae, *Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis* geminate from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsensis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum,*

*Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species; *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; Deroceras (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae Helicigona arbustorum); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as 6-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose,* or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF—YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | Agrilus planipennis | Ash |
| Cerambycidae | Anoplura glabripennis | Hardwoods |
| Scolytidae | Xylosandrus crassiusculus | Hardwoods |
| | X. mutilatus | Hardwoods |
| | Tomicus piniperda | Conifers |

TABLE B

Examples of native woodborers of economic importance.

| Family | Species | Host or Crop Infested |
|---|---|---|
| Buprestidae | Agrilus anxius | Birch |
| | Agrilus politus | Willow, Maple |
| | Agrilus sayi | Bayberry, Sweetfern |
| | Agrilus vittaticolllis | Apple, Pear, Cranberry, Serviceberry, Hawthorn |
| | Chrysobothris femorata | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | Texania campestris | Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |

TABLE B-continued

Examples of native woodborers of economic importance.

| Family | Species | Host or Crop Infested |
|---|---|---|
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp.,

*Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodexspp., Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents. The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl-hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/ alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mpt" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated.

LCMS Methods:

Method A:

Spectra were recorded on a Mass Spectrometer from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+ 0.05% HCOOH, B=Acetonitrile+0.05% HCOOH, gradient: 10-100% B in 1.2 min; Flow (ml/min) 0.85.

Example P1: 3-ethylsulfonyl-2-[7-(trifluoromethyl) imidazo[1,2-c]pyrimidin-2-yl]quinolone (compound P1, Table P)

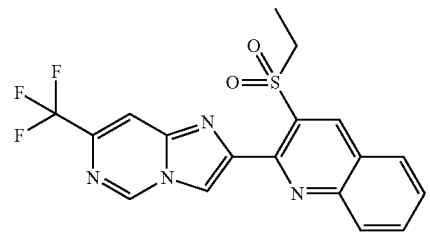

(Compound P1, Table P)

Step A: Ethyl 3-ethylsulfanylquinoline-2-carboxylate

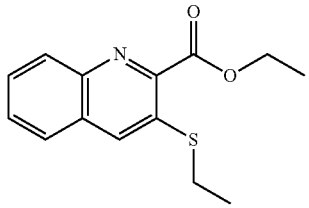 [SMILES: CCOC(=O)c1nc2ccccc2cc1SCC]

To stirred solution of ethyl 3-aminoquinoline-2-carboxylate (3.6 g, 16.66 mmol, prepared as described in WO 2011093365) and diethyldisulfide (4.51 ml, 36.6 mmol), in dichloroethane (30 ml) was added t-butyl nitrite dropwise at ambient temperature. The reaction mixture was heated to 40° C. for 2 hours. After reaction completion (TLC analysis) the reaction mixture was diluted with dichoromethane and washed with water (2×10 mL). The combined organic layers were dried over $Na_2SO_4$, filtered, and concentrated in vacuo. The crude was purified by flash chromatography over silica gel to give the title compound as a yellow liquid.

$^1$H NMR (400 MHz, $CDCl_3$): δ (ppm): 8.14 (d, 1H); 8.06 (s, 1H); 7.75 (d, 1H); 7.68 (m, 1H); 7.58 (m, 1H); 4.54 (q, 2H); 3.03 (q, 2H); 1.48 (t, 3H) 1.40 (t, 3H).

Step B: 3-ethylsulfanylquinoline-2-carboxylic acid

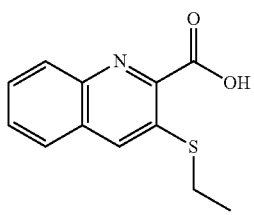 [SMILES: CCSc1cc2ccccc2nc1C(=O)O]

To as stirred solution of ethyl 3-aminoquinoline-2-carboxylate (1 g, 3.8 mmol) in THF (8 ml) was added NaOH (2 N, 8.36 mmol) at room temperature. The reaction mixture was stirred for 16 hours at ambient temperature. After reaction completion (TLC analysis) the reaction mixture was extracted with ethyl acetate (2×10 mL). The aqueous phase was then acidified to pH=4 with 10% citric acid solution and extracted with ethyl acetate (3×20 ml). The combined organic extracts were dried over $Na_2SO_4$, filtered, and concentrated in vacuo. Trituration with ether gave the desired title compound as yellow solid.

$^1$H NMR (400 MHz, DMSO-$d_6$): δ (ppm): 13.7 (s, 1H); 8.42 (s, 1H); 8.00 (m, 2H); 7.75 (m, 1H); 7.68 (m, 1H); 3.09 (q, 2H); 1.29 (t, 3H).

Step C: 3-ethylsulfanyl-N-methoxy-N-methyl-quinoline-2-carboxamide

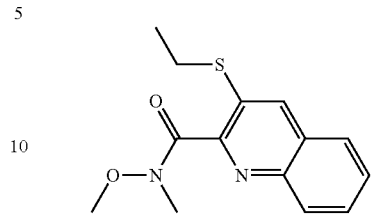

3-Ethylsulfanylquinoline-2-carboxylic acid (0.8 g, 3.43 mmol) was dissolved in dichloromethane (12 mL) under an argon atmosphere. To this were added 2 drops of dimethylformamide and then oxallyl chloride (0.3889 mL, 4.458 mmol). The reaction was stirred for 3 hours at room temperature by which time LCMS analysis of a aliquot treated with MeOH showed complete conversion to 3-ethylsulfanylquinoline-2-carbonyl chloride had occurred. The reaction mixture was concentrated in vacuo and used without further purification in the next step.

A solution of N-methoxymethanamine hydrochloride (0.3345 g, 3.429 mmol) in dichloromethane (13 mL) and triethylamine (1.67 mL, 12.00 mmol) was cooled to 0° C. and treated with 3-ethylsulfanylquinoline-2-carbonyl (0.863 g, 3.429 mmol) dissolved in 3 ml of dichloromethane at 0° C.

Reaction mixture was allowed to warm to room temperature and stirred for 30 min. LCMS analysis after this time showed reaction completion. The reaction mixture was diluted with saturated aqueous $NH_4Cl$, and the aqueous layer was extracted 3 times with dichloromethane. The combined organic layers were washed successively with water and brine, dried over $Na_2SO_4$, filtered and concentrated in vacuo to give the crude product. This was purified by flash chromatography with a column of 24 g and a gradient cyclohexane+0-100% ethyl acetate to give the title product as a yellow oil.

$^1$H NMR (400 MHz, CHLOROFORM-d) δ ppm: 1.34 (t, J=7.34 Hz, 3H); 3.03 (q, J=7.34 Hz, 2H); 3.46 (s, 3H); 3.57 (s, 3H); 7.55-7.62 (m, 1H); 7.68-7.74 (m, 1H); 7.79 (d, J=8.44 Hz, 1H); 8.10 (d, J=8.44 Hz, 1H); 8.17 (s, 1H).

LCMS (method 1); Rt=0.87 min, [M+H] 277.

Step D: 1-(4-ethylsulfanyl-3-isoquinolyl)ethanone

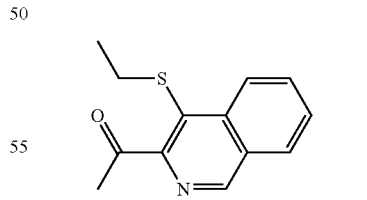

A solution of bromo(methyl)magnesium (1.4 M in THF:Toluene 1:3 ((1.9 mL, 2.605 mmol) in dry toluene (9 mL) was cooled to 0° C. and treated with 3-ethylsulfanyl-N-methoxy-N-methyl-quinoline-2-carboxamide (0.6 g, 2.171 mmol) dissolved in 3 ml of toluene. The reaction mixture was stirred for 1 hour at 0° C. and then 1 hour at room temperature. LCMS analysis after this time showed reaction completion. The reaction mixture was slowly quenched with saturated aqueous $NH_4Cl$ and HCl 10% (15 ml) and the resulting mixture vigorously stirred for 15 min at room temperature. The aqueous layer was extracted with ethyl acetate and the combined organic phases washed successively with 10% HCl aq sol, water and brine, dried over Na$_2$SO$_4$, filtered and concentrated in vacuo. The crude product was purified by flash chromatography with a column of 12 g and a gradient cyclohexane+0-80% ethyl acetate to give the title compound as a yellow solid.

$^1$H NMR (400 MHz, CHLOROFORM-d) 6 ppm: 1.46 (t, J=7.34 Hz, 3H); 2.87 (s, 3H); 3.04 (q, J=7.34 Hz, 2H); 7.58-7.65 (m, 1H); 7.65-7.71 (m, 1H); 7.76 (d, J=6.60 Hz, 1H); 7.99 (s, 1H); 8.10 (d, J=8.44 Hz, 1H).

LCMS (method 1); Rt=1.04 min, [M+H] 232.

Step E: 1-(4-ethylsulfonyl-3-isoquinolyl)ethanone

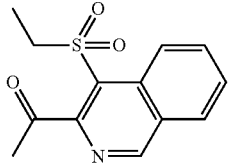 [SMILES: CCS(=O)(=O)c1c(C(C)=O)ncc2ccccc12]

A solution of 1-(4-ethylsulfanyl-3-isoquinolyl)ethanone (0.375 g, 1.621 mmol) in dichloromethane (8 mL) was cooled to 0° C. and treated with meta-chloroperbenzoic acid (0.8393 g, 3.405 mmol). The reaction was stirred 30 min at 0° C. and then warmed to room temperature and stirred for 1 hr. LCMS analysis after this time showed reaction completion. The reaction mixture was quenched with NaOH 1 M (10 ml) and sodium thiosulfate aqueous solution (5 ml). The aqueous layer was extracted 3 times with dichloromethane and the combined organic phases washed successively with NaOH 1 M, brine, dried over Na$_2$SO$_4$, filtered and concentrated in vacuo, to give the title product as a white solid. This was used in the next step without further purification.

$^1$H NMR (400 MHz, CHLOROFORM-d) 6 ppm: 1.39 (t, J=7.34 Hz, 3H); 2.85 (s, 3H); 3.68 (q, J=7.46 Hz, 2H); 7.74-7.81 (m, 1H); 7.98 (ddd, J=8.53, 7.06, 1.28 Hz, 1H); 8.04 (d, J=8.44 Hz, 1H); 8.22 (d, J=8.07 Hz, 1H); 8.91 (s, 1H).

LCMS (method 1); Rt=0.84 min, [M+H] 264.

Step F: 2-bromo-1-(3-ethylsulfonyl-2-quinolyl)ethanone

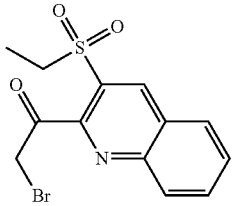 [SMILES: CCS(=O)(=O)c1cc2ccccc2nc1C(=O)CBr]

1-(4-Ethylsulfonyl-3-isoquinolyl)ethanone (0.4 g, 1.519 mmol) was dissolved in chloroform (2 mL) and ethyl acetate (2 mL) in microwave vial and treated with copper(II) bromide (0.6786 g, 3.038 mmol). The reaction mixture was then stirred in the microwave for 1 h at 140° C. After this time the reaction mixture was dissolved in dichloromethane, dried over Na$_2$SO$_4$, filtered and concentrated in vacuo. This was purified by flash chromatography over silicagel to give the title compound as a white solid.

$^1$H NMR (400 MHz, CHLOROFORM-d) 6 ppm: 1.41 (t, J=7.52 Hz, 3H); 3.71 (q, J=7.46 Hz, 2H); 4.96 (s, 2H); 7.79-7.87 (m, 1H); 8.01 (ddd, J=8.53, 7.06, 1.28 Hz, 1H); 8.07 (d, J=8.07 Hz, 1H); 8.24 (d, J=8.44 Hz, 1H); 8.97 (s, 1H).

LCMS (method 1); Rt=0.93 min, [M−H] 342/344.

Step G: 3-ethylsulfonyl-2-[7-(trifluoromethyl)imidazo[1,2-c]pyrimidin-2-yl]quinolone (compound P1, Table P)

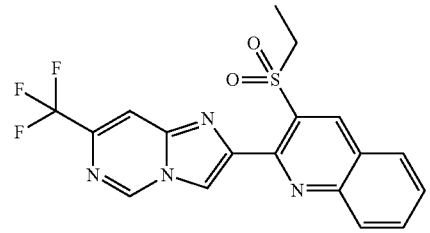

(compound P1, Table P)

In a microwave vial, 6-(trifluoromethyl)pyrimidin-4-amine (0.09532 g, 0.5845 mmol) and 2-bromo-1-(3-ethylsulfonyl-2-quinolyl)ethanone (0.2 g, 0.5845 mmol) dissolved in acetonitrile (7 mL) were stirred and heated for 1 hour at 150° C. After this time, the reaction mixture was evaporated and the resultant solid dissolved in dichloromethane and washed with NaHCO$_3$ sat sol. The organic layer was then washed with brine, dried over Na$_2$SO$_4$, filtered and concentrated in vacuo. Purification by flash chromatography with a column of 12 g and a gradient of dichloromethane+0-10% ethylacetate gave the title compound as a white solid.

$^1$H NMR (400 MHz, CHLOROFORM-d) δ ppm 1.40 (t, J=7.34 Hz, 3H); 3.96 (q, J=7.34 Hz, 2H); 7.77 (t, J=7.52 Hz, 1H); 7.92-8.01 (m, 1H); 8.01 (s, 1H); 8.09 (d, J=8.44 Hz, 1H); 8.25 (d, J=8.44 Hz, 1H); 8.43 (s, 1H); 9.12 (s, 1H); 9.24 (s, 1H).

LCMS (method 1); Rt=0.91 min, [M+H] 407.

Example P2: 2-[6-ethylsulfonyl-1-methyl-2-(trifluoromethyl)benzimidazol-5-yl]-7-(trifluoromethyl)imidazo[1,2-c]pyrimidine (compound P2, Table P)

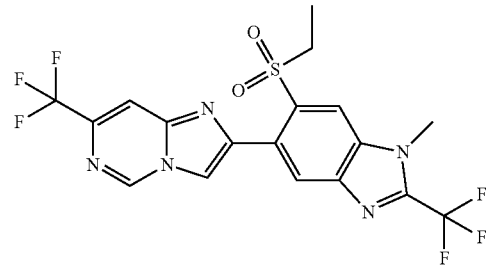

Step A: 4-chloro-2-ethylsulfanyl-5-nitro-benzoic acid

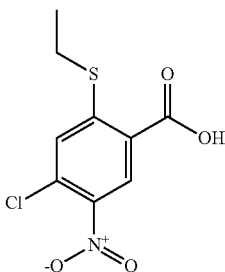

To a solution of 4-chloro-2-fluoro-5-nitro-benzoic acid (20 g, 91.095 mmol, commercially available, CAS [35112-05-1]) in 1-Methyl-2-pyrrolidone (250 mL) at 90° C. was added sodium t-butoxide (9.6302 g, 100.20 mmol). After 10 min ethylsulfanylsodium (9.366 g, 100.20 mmol) was added and the reaction mixture stirred at 90° C. for two hours. After this time, the reaction mixture was poured onto water (1 L) and the acifified to pH 1 with conc. hydrochloride acid. A precipitate was formed and was filtered and then suspended in diethyl ether and filtered. The solid was formed was filtered and shown to be pure 2,4-bis(ethylsulfanyl)-5-nitro-benzoic acid. The filtrate was concentrated in vacuo to give the title compound.

$^1$H NMR (300 MHz, CDCl$_3$) ppm 13.84 (s, 1H) 8.52 (s, 1H); 7.6 (s, 1H); 3.09 (q, 2H); 1.3 (t, 3H).

LC-MS (Method A): RT 1.00 min (260, MH$^-$) (262, MH$^+$).

Step B: Synthesis of 2-ethylsulfanyl-4-(methylamino)-5-nitro-benzoic acid

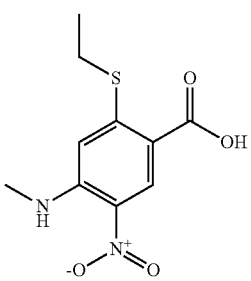

To a solution of 4-chloro-2-ethylsulfanyl-5-nitro-benzoic acid (8.9 g, 34 mmol) in tetrahydrofuran (20 mL, 244 mmol) was added dropwise methylamine (2 mol/L) in tetrahydrofurane (100 mL, 200 mmol). The mixture was stirred overnight at ambient temperature. LCMS analysis showed only minor conversion to the desired product, and then the suspension was transferred to an autoclave, 30 mL of methylamine 2N was added, and the reaction was stirred at 80° C. for 5 hours. After this time a further 20 mL of 2N methylamine was added then the reaction was stirred in an autoclave for two days. The reaction mixture was concentrated in vacuo and the residue taken up in water, which was made basic with sodium hydroxide 1N, and then extracted with ethyl acetate. The water phase was acidified with hydrochloride acid conc. 37% and extracted with ethyl acetate. All organic layers were combined, dried over magnesium sulfate, and concentrated in vacuo. The residue was purified by flash chromatography to give the title compound as a yellow-brownish solid.

$^1$H NMR (300 MHz, CDCl$_3$) ppm 12.87 (s, 1H) 8.68 (s, 1H); 6.55 (s, 1H); 3.05 (s, 3H); 3.00 (q, 2H) 1.33 (t, 3H).

LC-MS (Method A): RT 1.04 min (257, MH$^+$).

Step C: 6-Ethylsulfanyl-1-methyl-2-(trifluoromethyl)benzimidazole-5-carboxylic acid

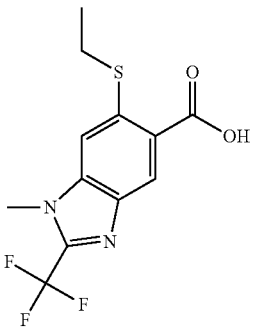 [SMILES: CCSc1cc2c(cc1C(=O)O)nc(C(F)(F)F)n2C]

To a solution of 2-ethylsulfanyl-4-(methylamino)-5-nitro-benzoic acid (0.300 g, 1.17 mmol) in 2,2,2-trifluoroacetic acid (10 mL, 129 mmol) at 0° C., zinc (0.260 g, 3.98 mmol) was added and cooling bath was removed. After 30 min, reduction of the nitro group was complete according to LC/MS and a small amount of the title compound was observed. The brown solution was then heated at 70° C. product for 1 hr after which time LCMS showed reaction completion. The mixture was concentrated to the half of its volume, and then poured into water and extracted with ethyl acetate. The organic phase was washed with water and brine, dried over magnesium sulfate and concentrated in vacuo. The residue was purified by flash chromatography to give the title compound.

$^1$H NMR (300 MHz, CDCl$_3$) ppm 13.03 (s, 1H) 8.30 (s, 1H); 7.64 (s, 1H); 4.00 (s, 3H); 3.06 (q, 2H) 1.32 (t, 3H).

LC-MS (Method A): RT 1.06 min (303, MH$^-$) (305, MH$^+$).

Step D: Synthesis of 6-ethylsulfanyl-N-methoxy-N,1-dimethyl-2-(trifluoromethyl) benzimidazole-5-carboxamide

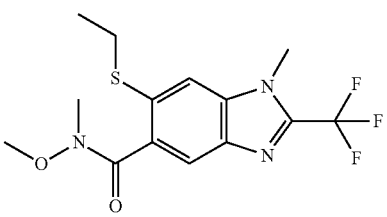 [SMILES: CCSc1cc2c(cc1C(=O)N(C)OC)nc(C(F)(F)F)n2C]

A solution of 6-ethylsulfanyl-1-methyl-2-(trifluoromethyl)benzimidazole-5-carboxylic acid (0.70 g, 2.3 mmol) in dichloromethane (11 mL) was treated with dimethylformamide (2 drops) and then oxalyl chloride (0.26 mL, 3.0 mmol) was added (formation of gas) and the reaction mixture was stirred at room temperature overnight. After 16 hours, 0.2 ml oxalyl chloride was added and no more gas evolution was observed. The reaction mixture was evaporated to give 6-ethylsulfanyl-1-methyl-2-(trifluoromethyl)benzimidazole-5-carbonyl chloride which was used without further purification. A suspension of N-methoxymethanamine hydrochloride (0.23 g, 2.3 mmol) in dichloromethane (11 mL) was treated with triethylamine (1.1 mL, 8.0 mmol). The reaction mixture was cooled to 0° C. and 6-ethylsulfanyl-1-methyl-2-(trifluoromethyl)benzimidazole-5-carbonyl chloride (0.74 g, 2.3 mmol) dissolved in 3 ml of dichloromethane was added slowly at this temperature. The reaction mixture was stirred 1.5 hours at 0° C. LC-MS analysis showed the formation of desired product. The reaction mixture was allowed to warm to room temperature and quenched with water. The organic layer was separated and aqueous layer was extracted 2 times with dichloromethane. The combined organic layer was dried over $Na_2SO_4$, filtered and concentrated in vacuo. The crude product was purified over silica gel cartridge to give the title compound.

$^1$H NMR (400 MHz, Chloroform-d) δ ppm 1.30 (t, J=7.34 Hz, 3H) 3.00 (q, J=7.34 Hz, 2H) 3.34 (br. s., 3H) 3.44-3.58 (br. S., 3H) 3.96 (s, 3H) 7.53 (s, 1H) 7.82 (s, 1H).

LC-MS (Method A) M+H (348); Rt=0.87 min.

Step E: 1-[6-Ethylsulfanyl-1-methyl-2-(trifluoromethyl)benzimidazol-5-yl]ethanone

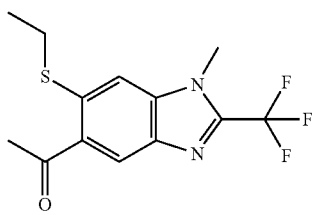 [SMILES: CCSc1cc2c(cc1C(C)=O)nc(C(F)(F)F)n2C]

In three neck flask under argon, methylmagnesium bromide 1.4 mol/L in THF/Toluene (1:3) (1.4 mL, 1.9 mmol) was diluted in toluene (8.4 mL). The solution was cooled to 0° C. and 6-ethylsulfanyl-N-methoxy-N,1-dimethyl-2-(trifluoromethyl)benzimidazole-5-carboxamide (0.56 g, 1.6 mmol), dissolved in 5 ml of toluene and 2 ml of THF was added dropwise. The reaction mixture was stirred 1 hour at 0° C. and 1 hour at room temperature. LC-MS analysis showed the presence of starting material in the reaction mixture. The solution was cooled down again to 0° C. and methylmagnesium bromide (1.4 mL, 1.9 mmol) was added again. After 2 hours at room temperature LC-MS showed completion of reaction.

The crude was slowly quenched with $NH_4Cl$ sat aq (10 ml) and HCl 1 M (5 ml) and resulting mixture was vigorously stirred for 1 hour at room temperature. The aqueous layer was extracted twice with ethylacetate. The combined organic phases were washed with 1 M HCl aq sol, water and brine, dried over $Na_2SO_4$ anhydrous, filtered and concentrated in vacuo. The crude product was purified by flash chromatography over silica gel cartridge to give the title compound as a beige solid.

1H NMR (400 MHz, CHLOROFORM-d) δ ppm 1.42 (t, J=7.34 Hz, 3H) 2.69 (s, 3H) 2.99 (q, J=7.34 Hz, 2H) 3.95 (d, J=0.73 Hz, 3H) 7.30 (s, 1H) 8.31 (s, 1H) LC-MS (Method A) M+H (303); Rt=0.95 min.

Step F: 1-[6-Ethylsulfonyl-1-methyl-2-(trifluoromethyl)benzimidazol-5-yl]ethanone

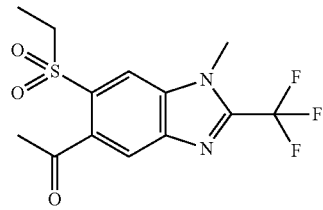 [SMILES: CCS(=O)(=O)c1cc2c(cc1C(C)=O)nc(C(F)(F)F)n2C]

At 0° C. MCPBA (0.20 g, 0.88 mmol) was added portionwise to a solution of 1-[6-ethylsulfanyl-1-methyl-2-(trifluoromethyl)benzimidazol-5-yl]ethanone (0.13 g, 0.43 mmol) in chloroform (3.9 mL). By adding of the first portion, there was a small exothermic reaction. Temperature was increased until 12° C. The beige suspension was stirred at room temperature. After 5 days LC/MS analysis showed the formation of desired mass. Saturated sodium thiosulfate aqueous solution (lightly exothermic) and $NaHCO_3$ aq were added and the mixture was stirred at room temperature for 40 min. Organic layer was separated, washed again with $NaHCO_3$ aq and dried over $Na_2SO_4$, filtered and concentrated in vacuo at 40° C. to give the crude product containing mainly 1-[6-ethylsulfonyl-1-methyl-2-(trifluoromethyl)benzimidazol-5-yl]ethanone. This was used in the next step without further purification.

$^1$H NMR (400 MHz, CHLOROFORM-d) δ ppm 1.35 (t, J=7.34 Hz, 3H) 2.72 (s, 3H) 3.55 (q, J=7.46 Hz, 2H) 4.07 (s, 3H) 7.99 (s, 1H) 8.25 (s, 1H).

LC-MS (Method A) M+H (335); Rt=0.83 min

Step G: 2-Bromo-1-[6-ethylsulfonyl-1-methyl-2-(trifluoromethyl)benzimidazol-5-yl]ethanone

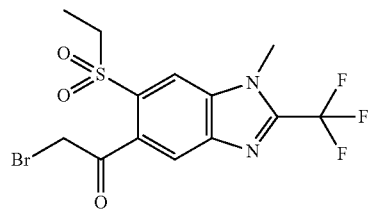 [SMILES: CCS(=O)(=O)c1cc2c(cc1C(=O)CBr)nc(C(F)(F)F)n2C]

1-[6-ethylsulfonyl-1-methyl-2-(trifluoromethyl)benzimidazol-5-yl]ethanone (0.30 g, 0.90 mmol) was dissolved in chloroform (1.5 mL) and ethylacetate (1.5 mL) in a microwave vial and dibromocopper (0.40 g, 1.8 mmol) was added. The reaction mixture was stirred in the microwave for 55' at 140° C. LC-MS analysis showed the formation of desired product, starting material and by-product. Reaction mixture was filtered and precipitate was washed with dichloromethane, then the filtrate was concentrated in vacuo. The crude obtained was purified by flash chromatography to give mainly 2-bromo-1-[6-ethylsulfonyl-1-methyl-2-(trifluoromethyl)benzimidazol-5-yl]ethanone but also starting material and by-product. The mixture was used for the next step without further purification.

LC-MS (Method A) M+H (413-415); Rt=0.90 min

Step H: 2-[6-ethylsulfonyl-1-methyl-2-(trifluoromethyl)benzimidazol-5-yl]-7-(trifluoromethyl)imidazo[1,2-c]pyrimidine

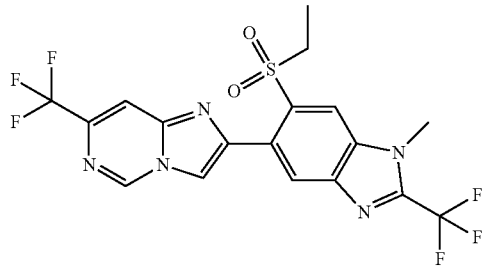 [SMILES: CCS(=O)(=O)c1cc2c(cc1-c1cn3cnc(C(F)(F)F)cc3n1)nc(C(F)(F)F)n2C]

In a microwave vial 2-bromo-1-[6-ethylsulfonyl-1-methyl-2-(trifluoromethyl)benzimidazol-5-yl]ethanone (0.25 g, 0.61 mmol) and 6-(trifluoromethyl)pyrimidin-4-amine (0.10 g, 0.61 mmol) were dissolved in acetonitirle (3.0 mL). The vial was stirred 1 h at 150° C. in the microwave system. LC-MS analysis showed the formation of the desired product. The reaction mixture was evaporated in vacuo. The residue was dissolved in dichloromethane and washed with NaHCO₃ (10 mL) sat sol with 1 mL of NH₄OH 1N. The organic layer was washed with brine, dried over Na₂SO₄, filtered and concentrated in vacuo. The crude product was purified by flash chromatography over silica gel cartridge to give a mixture of starting material and desired product. A second purification had to be done and then the mixture obtained was purified by reverse phase to give the title compound as a white solid.

1H NMR (400 MHz, Chloroform-d) δ ppm 1.26 (t, J=7.34 Hz, 3H) 3.54 (q, J=7.46 Hz, 2H) 4.11 (s, 3H) 7.96 (s, 1H) 8.12 (d, J=6.24 Hz, 2H) 8.43 (s, 1H) 9.18 (s, 1H).

LC-MS (Method A) M+H (478); Rt=0.95 min

Example P3: Synthesis of 6-ethylsulfonyl-1-methyl-2-(trifluoromethyl)-5-[7-(trifluoromethyl)imidazo[1,2-a]pyridin-2-yl]benzimidazole (Compound P3, Table P)

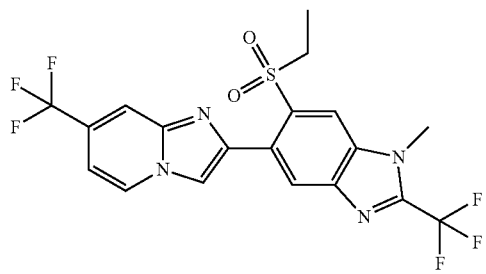 [SMILES: CCS(=O)(=O)c1cc2c(cc1-c1cn3ccc(C(F)(F)F)cc3n1)nc(C(F)(F)F)n2C]

4-(trifluoromethyl)pyridin-2-amine (0.15 g, 0.90 mmol), 1-[6-ethylsulfonyl-1-methyl-2-(trifluoromethyl)benzimidazol-5-yl]ethanone (0.15 g, 0.45 mmol, step F, Example P2)), o-phenanthroline monohydrate (0.016 g, 0.090 mmol), diiodozinc (0.029 g, 0.090 mmol), diacetoxycopper hydrate (0.018 g, 0.090 mmol) and 1,2-dichlorobenzene (1.5 mL) were put in a flask. The beige suspension was stirred at 120° C. overnight.

After 15 hours the reaction mixture was allowed to cool down to rt. LC/MS analysis showed the mass of the desired product. Dichloromethane was added, the mixture was filtered and the residue was washed with dichloromethane and methanol. The mother liquid was evaporated (contains still dichlorobenzene).

The crude obtained was purified by flash chromatography over silica gel and then by reverse phase chromatography to give the title compound as a white solid.

1H NMR (400 MHz, Chloroform-d) δ ppm 1.21-1.27 (t, 3H) 3.51 (q, J=7.34 Hz, 2H) 4.10 (s, 3H) 7.05 (dd, J=7.15, 1.65 Hz, 1H) 7.96 (s, 1H) 8.06 (s, 1H) 8.13 (s, 1H) 8.31 (d, J=7.34 Hz, 1H) 8.43 (s, 1H).

LC/MS (method A) M+H[477]; Rt=0.99 min

Example P4: 2-[6-ethylsulfonyl-1-methyl-2-(trifluoromethyl)benzimidazol-5-yl]-7-(trifluoromethylsulfanyl)imidazo[1,2-c]pyrimidine (Compound P4, Table P)

(Compound P4, Table P)

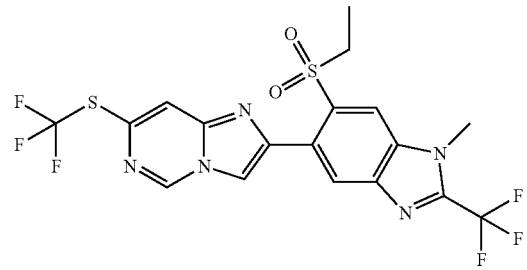

Step A:
6-(Trifluoromethylsulfanyl)pyrimidin-4-amine

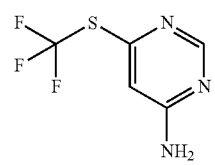 [SMILES: Nc1cc(SC(F)(F)F)ncn1]

To a solution of 6-bromopyrimidin-4-amine (1.75 g, 10 mmol) in dry acetonitrile (45 mL) was added (bpy)CuSCF3 (4.8 g, 15 mmol). The mixture was refluxed at 100° C. for 2 hours under a nitrogen atmosphere. After this time, the mixture was filtered and concentrated in vacuo. The crude product was purified by column chromatography on silica gel to give the product 6-((trifluoromethyl)thio)pyrimidin-4-amine.

¹H-NMR (400 Mz, DMSO-d6) δ: 6.60 (s, 1H), 7.26 (s, 2H), 8.29 (s, 1H).

¹⁹F-NMR (300 Mz, DMSO-d6) δ: −42.45 (s, 3F).

Step B: Synthesis of 2-[6-ethylsulfonyl-1-methyl-2-(trifluoromethyl)benzimidazol-5-yl]-7-(trifluoromethylsulfanyl)imidazo[1,2-c]pyrimidine (Compound P4, Table P)

(Compound P4, Table P)

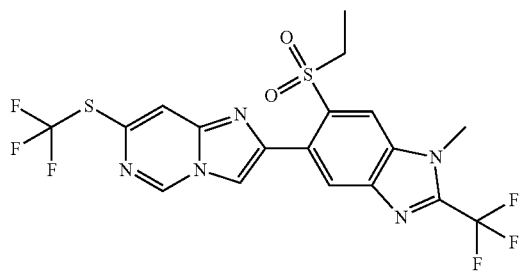 [SMILES: CCS(=O)(=O)c1cc2c(cc1-c1cn3cnc(SC(F)(F)F)cc3n1)nc(C(F)(F)F)n2C]

In a microwave vial 2-bromo-1-[6-ethylsulfonyl-1-methyl-2-(trifluoromethyl)benzimidazol-5-yl]ethanone (0.13 g, 0.31 mmol, Step G, example P2) and 6-(trifluoromethylsulfanyl)pyrimidin-4-amine (0.061 g, 0.31 mmol) were dissolved in acetonitrile (1.6 mL). The vial was stirred 1 hour at 150° C. in the microwave. The LC-MS analysis showed the formation of desired product. The reaction mixture was evaporated and the crude obtained was purified by flash chromatography over silica gel and then by reverse phase chromatography to give the title compound.

$^1$H NMR (400 MHz, CHLOROFORM-d) δ ppm 1.29 (t, J=1.00 Hz, 3H) 3.5 (q, J=7 Hz, 2H) 4.1 (s, 3H) 8.0 (s, 1H) 8.1 (s, 1H) 8.2 (s, 1H) 8.5 (s, 1H) 9.1 (d, J=1 Hz, 1H)

LC/MS (method A) M+H [510]; Rt=1.00 min

TABLE P

Examples of compounds of formula (I) Prepared and Physical and Spectroscopic Data

| Compound No. | Compound | Melting Point | LCMS/NMR |
|---|---|---|---|
| P1 | | 233-235° C. | LCMS (method 1): 407 (M + H)$^+$ $R_t$ = 0.91 min |
| P2 | | 242-243° C. | LCMS (method 1): 478 (M + H)$^+$ $R_t$ = 0.95 min |
| P3 | | 259-260° C. | LCMS (method 1): 477 (M + H)$^+$ $R_t$ = 0.99 min |

TABLE P-continued

Examples of compounds of formula (I) Prepared and Physical and Spectroscopic Data

| Compound No. | Compound | Melting Point | LCMS/NMR |
|---|---|---|---|
| P4 | (structure shown) | — | LCMS (method 1): 510 (M + H)$^+$<br>R$_t$ = 1.00 min |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 to 3 and P of the present invention"):

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 23 and P of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+

TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex(1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin 11 (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-01 with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure Ill (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulfon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin 1 (696)+TX, jasmolin 11 (696)+TX, jodfenphos (1248)+TX, juvenile hormone I [CCN]+TX, juvenile hormone II [CCN]+TX, juvenile hormone Ill [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin 11 (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, fluxametamide (WO 2007/026965)+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2](free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-

21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a, 12b-decahydro-6,12-dihydroxy-4,6a, 12b-trimethyl-11-oxo-9-(3-pyridinyl)-2H, 11H naphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, flufiprole [704886-18-0]+TX, cyclaniliprole [1031756-98-5]+TX, tetraniliprole [1229654-66-3]+TX, guadipyr (described in WO2010/060231)+TX and cycloxaprid (described in WO 2005/077934)+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®, BioNem-WP®, VOTVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis* kurstaki (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis* kurstaki BMP 123 (Baritone®)+TX, *Bacillus thuringiensis* kurstaki HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis* tenebrionis (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus* humicola+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigi*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, Muscodorroseus strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (BioSave®)+TX, *Pseudomonas viridiflava*+TX, *Pseudomons fluorescens* (Zequanox)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®)+TX; and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable pheromone®)+TX, Peachtree Borer Pheromone (Isomate-P®)+TX, Tomato Pinworm Pheromone (3M Sprayable pheromone®)+TX, Entostat powder (extract from palm tree) (Exosex CM®)+TX, Tetradecatrienyl acetate+TX, 13-Hexadecatrienal+TX, (E+TX,Z)-7+TX, 9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex+TX, Bugline cucumeris®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (TH RYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-II+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline sf®+TX, Scia-rid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetorole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used. "CAS Reg. No" means the Chemical Abstracts Registry Number.

The active ingredient mixture of the compounds of formula I selected from Table 1 to 3 and P with active ingredients described above comprises a compound selected from Table 1 to 3 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practiced on the human or animal body.

The mixtures comprising a compound of formula I selected from Table 1 to 3 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 to 3 and P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

BIOLOGICAL EXAMPLES

Example B1: *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1 and P2.

Example B2: *Euschistus heros*(Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1 and P2.

Example B3: *Myzus persicae* (Green Peach Aphid):Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compound resulted in at least 80% mortality at an application rate of 200 ppm: P1 and P2.

Example B4: *Myzus persicae* (Green Peach Aphid). Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compound resulted in at least 80% mortality at a test rate of 24 ppm: P2.

Example B5: *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
P1 and P2.

Example B6: *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compound resulted in at least 80% control at an application rate of 200 ppm: P1.

Example B6: *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compound gave an effect of at least 80% in at least one of the three categories (mortality, anti-feeding, or growth inhibition) at a test rate of 12.5 ppm: P1.

Example B7: *Frankliniella occidentalis* (Western Flower Thrips):Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compound resulted in at least 80% mortality at an application rate of 200 ppm: P2.

Example B8: *Thrips tabaci* (Onion Thrips) Feeding/Contact Activity

Sunflower leaf discs were placed on agar in 24-well microtiter plates and sprayed with aqueous test solutions prepared from 10'000 ppm DMSO stock solutions. After drying the leaf discs were infested with a thrips population of mixed ages. The samples were assessed for mortality 6 days after infestation.

The following compound resulted in at least 80% mortality at an application rate of 200 ppm: P2.

The invention claimed is:

1. A compound of formula I,

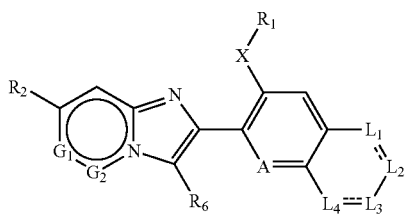

(I)

wherein
A is CH or N;
X is S, SO or $SO_2$;
$R_1$ is $C_1$-$C_4$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano, $C_1$-$C_4$ haloalkyl and $C_1$-$C_4$alkyl; or is $C_3$-$C_6$cycloalkyl-$C_1$-$C_4$alkyl mono- or polysubstituted by substituents selected from the group consisting of halogen, cyano, $C_1$-$C_4$ haloalkyl and $C_1$-$C_4$alkyl;
$R_2$ is hydrogen, halogen, $C_1$-$C_4$haloalkylsulfanyl, $C_1$-$C_4$haloalkylsulfinyl, $C_1$-$C_4$haloalkylsulfonyl, O($C_1$-$C_4$haloalkyl), —$SF_5$, C(O)O$C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$ haloalkyl and $C_1$-$C_4$alkyl;
$G_1$ is N or $CR_4$;
$G_2$ is N or $CR_5$, with the proviso that when $G_1$ is N, $G_2$ is $CR_5$;
$R_6$ is hydrogen, halogen or $C_1$-$C_4$alkyl;
$R_4$ and $R_5$, independently from each other, are hydrogen, halogen, cyano, nitro, $C_1$-$C_6$alkyl, $C_1$-$C_6$haloalkyl, or are $C_3$-$C_6$cycloalkyl which can be mono- or polysubstituted by $R_8$; or are $C_3$-$C_6$cycloalkyl-$C_1$-$C_4$alkyl which can be mono- or polysubstituted by $R_9$; or $R_4$ and $R_5$, independently from each other, are $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_4$haloalkylsulfonyl, $C_1$-$C_6$haloalkylsulfinyl or hydroxyl;
$R_8$ and $R_9$, independently from each other, are halogen, nitro, cyano, $C_1$-$C_4$haloalkoxy, $C_1$-$C_4$alkoxy $C_1$-$C_4$alkyl or $C_1$-$C_4$haloalkyl; and
$L_1$, $L_2$, $L_3$ and $L_4$ form together with the two carbon atoms to which $L_1$ and $L_4$ are attached, an aromatic, partially saturated carbocyclic or heterocyclic ring system;
wherein
$L_1$ is nitrogen, S(O)n, oxygen, N—$R_{10a}$ or C($R_{10a}$)$_m$;
$L_2$ is nitrogen, S(O)n, oxygen, N—$R_{10b}$, or C($R_{10b}$)$_m$;
$L_3$ is nitrogen, S(O)n, oxygen, N—$R_{10c}$, or C($R_{10c}$)$_m$;
$L_4$ is nitrogen, S(O)n, oxygen, a direct bond, N—$R_{10d}$ or C($R_{10d}$)$_m$; with the provisos that no more than 2 substituents selected from $L_1$, $L_2$, $L_3$ and $L_4$ can be oxygen or sulfur;
and if two L groups are oxygen, they are not adjacent to each other; and no more than three L groups can be nitrogen;
n is 0 to 2;
m is 1 or 2;
$R_{10a}$, $R_{10b}$, $R_{10c}$, and $R_{10d}$, independently from each other, are hydrogen, halogen, nitro, cyano, amino, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_4$alkoxy $C_1$-$C_4$alkyl, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_2$-$C_6$alkylcarbonyl, $C_2$-$C_6$alkoxycarbonyl, $C_2$-$C_6$ haloalkylcarbonyl, $C_2$-$C_6$haloalkoxycarbonyl, ($C_1$-$C_6$alkyl)NH, ($C_1$-$C_6$alkyl)$_2$N, ($C_1$-$C_6$cycloalkyl)NH, ($C_1$-$C_6$cycloalkyl)$_2$N, $C_1$-$C_6$alkylcarbonylamino, $C_1$-$C_6$cycloalkylcarbonylamino or —$SF_5$;
additionally one of $R_{10a}$, $R_{10b}$, $R_{10c}$ and $R_{10d}$ can be oxo; or
$R_{10a}$, $R_{10b}$, $R_{10c}$, and $R_{10d}$, independently from each other, are $C_3$-$C_6$cycloalkyl mono- or polysubstituted by substituents selected from the group consisting of $C_1$-$C_4$ haloalkyl, $C_1$-$C_4$alkyl and cyano; or
$R_{10a}$, $R_{10b}$, $R_{10c}$, and $R_{10d}$, independently from each other, are phenyl which can be mono- or polysubstituted by substituents selected from the group consisting of halogen, $C_1$-$C_4$ haloalkyl, $C_1$-$C_4$alkyl, $C_1$-$C_4$alkoxy and cyano; or an agrochemically acceptable salt, a stereoisomer, an enantiomer, a tautomer and an N-oxide of those compounds.

2. A compound of formula I according to claim 1 represented by the compounds of formula I-1

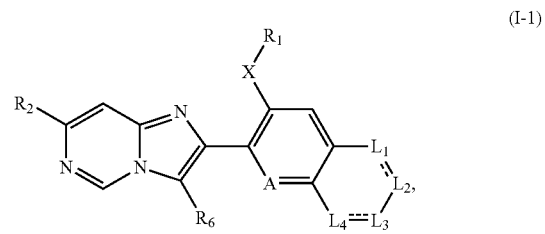

(I-1)

wherein the substituents X, A, $R_1$, $R_2$, $R_6$, $L_1$, $L_2$, $L_3$ and $L_4$ are as defined under formula I in claim 1.

3. A compound of formula I-1 according to claim 2, wherein

A is C—H or N;

$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;

X, $R_6$, $L_1$, $L_2$, $L_3$ and $L_4$ are as defined under formula I in claim 1; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

4. A compound of formula I according to claim 1 represented by the compounds of formula I-2

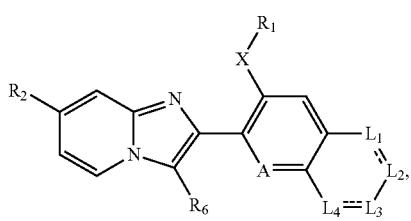
(I-2)

wherein the substituents X, A, $R_1$, $R_2$, $R_6$, $L_1$, $L_2$, $L_3$ and $L_4$ are as defined under formula I in claim 1.

5. A compound of formula I-2 according to claim 4, wherein

A is C—H or N;

$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;

X, $R_6$, $L_1$, $L_2$, $L_3$ and $L_4$ are as defined under formula I in claim 1; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

6. A compound of formula I according to claim 1 represented by the compounds of formula I-3;

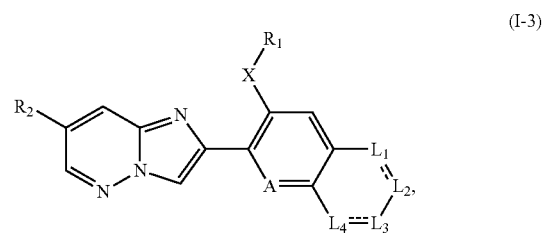
(I-3)

wherein the substituents X, A, $R_1$, $R_2$, $L_1$, $L_2$, $L_3$ and $L_4$ are as defined under formula I in claim 1.

7. A compound of formula I-3 according to claim 6, wherein

A is C—H or N;

$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;

X, $R_6$, $L_1$, $L_2$, $L_3$ and $L_4$ are as defined under formula I in claim 1; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

8. A compound of formula I-1a

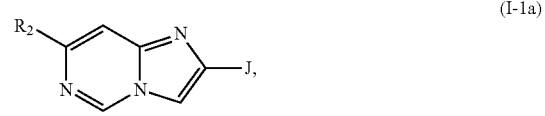
(I-1a)

111
wherein J is selected from the group J₁-J₂₇
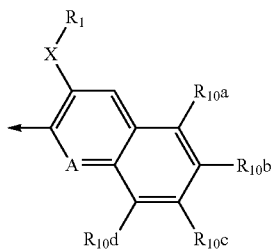
J₁
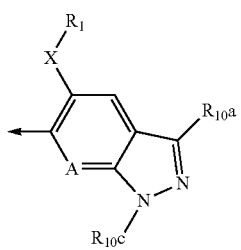
J₂
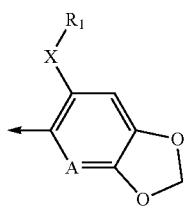
J₃
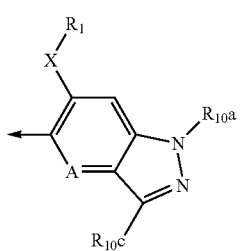
J₄
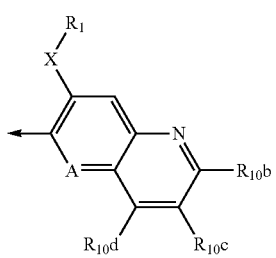
J₅
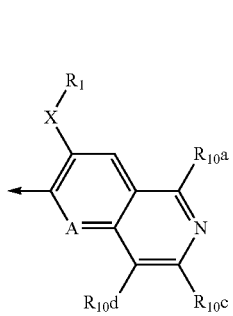
J₆
112
-continued
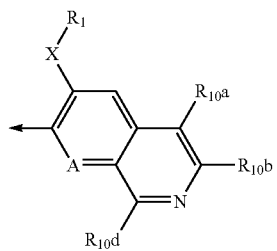
J₇
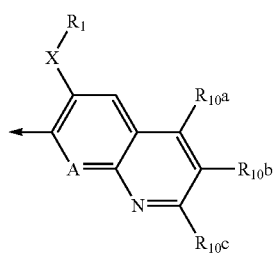
J₈
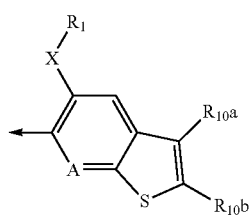
J₉
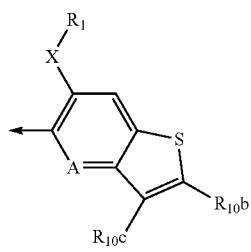
J₁₀
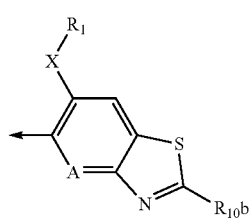
J₁₁
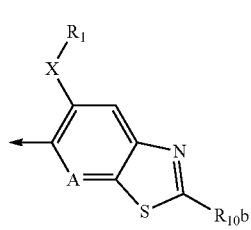
J₁₂

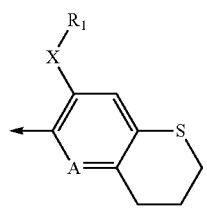
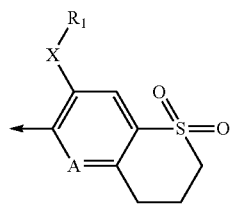
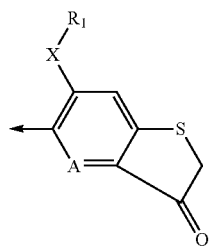
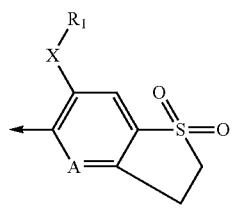
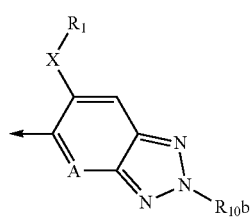
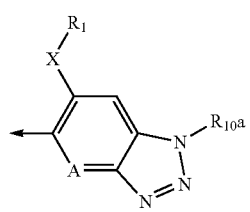
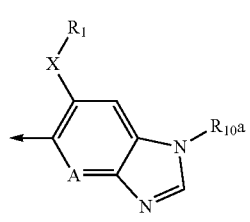
J13
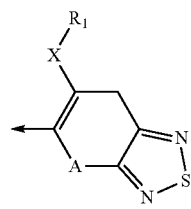
J14
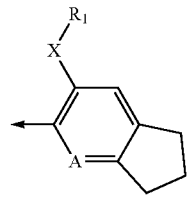
J15
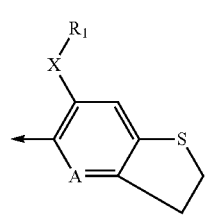
J16
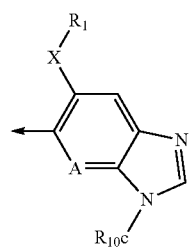
J17
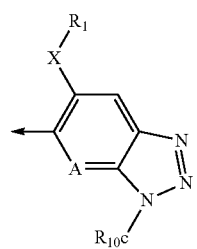
J18
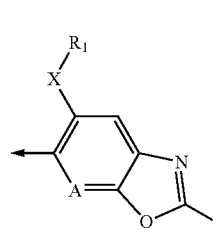
J19
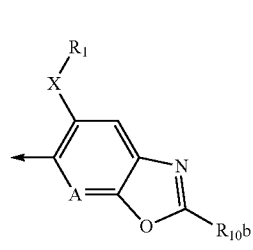
J20
J21
J22
J23
J24
J25
and
J26

J27
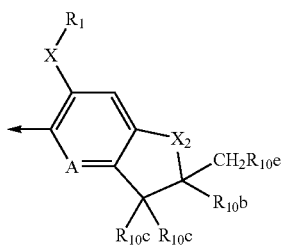
and A, R$_1$, R$_2$, X, R$_{10a}$, R$_{10b}$, R$_{10c}$, R$_{10d}$, are as defined in claim 3, and X$_2$ is oxygen or S(O)n$_1$, wherein n$_1$ is 0, 1, or 2, and R$_{10e}$ is hydrogen, C$_1$-C$_6$alkyl, C$_1$-C$_6$haloalkyl, 03-C$_6$cycloalkyl or C$_3$-C$_6$halocycloalkyl.
9. A compound formula I-2a
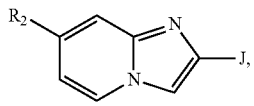
(I-2a)
wherein J is selected from the group J$_1$-J$_{27}$
J$_1$
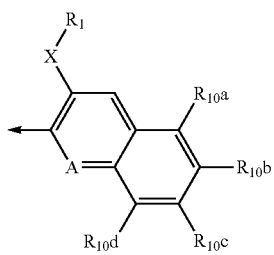
J$_2$
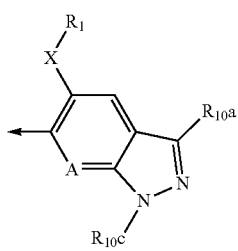
J$_3$
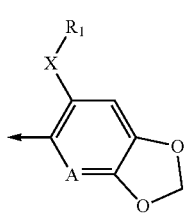
J$_4$
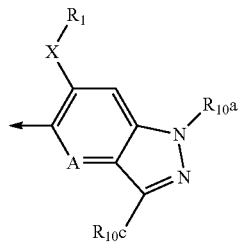
J$_5$
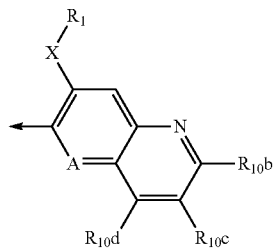
J$_6$
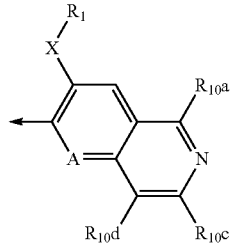
J$_7$
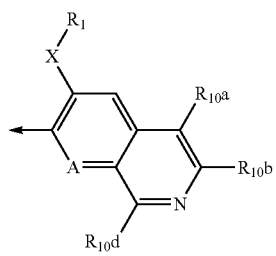
J$_8$
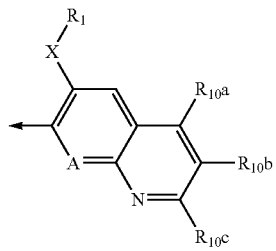
J$_9$
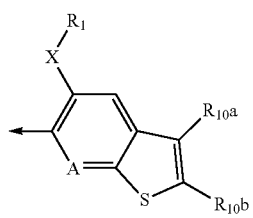

117
-continued
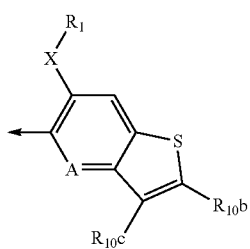
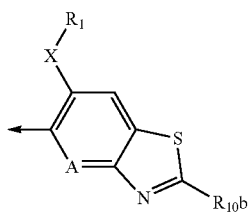
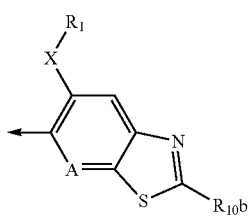
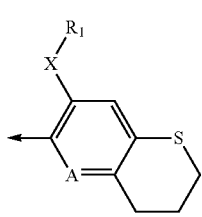
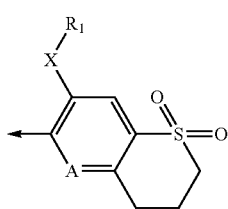
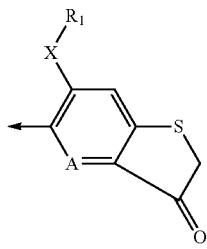
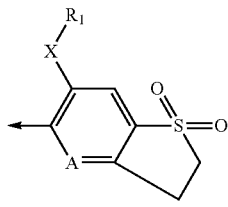
118
-continued
$J_{10}$
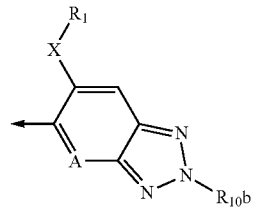
$J_{11}$
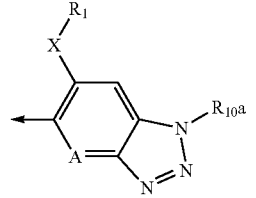
$J_{12}$
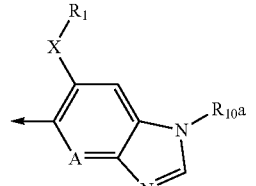
$J_{13}$
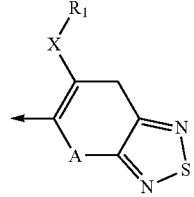
$J_{14}$
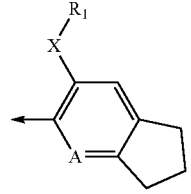
$J_{15}$
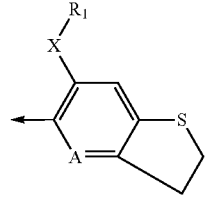
$J_{16}$
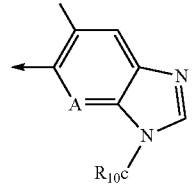
$J_{17}$
$J_{18}$
$J_{19}$
$J_{20}$
$J_{21}$
$J_{22}$
$J_{23}$ -continued
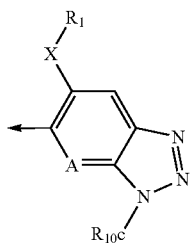
J₂₄
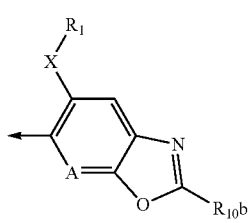
J₂₅
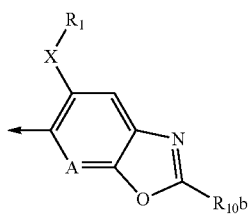
J₂₆
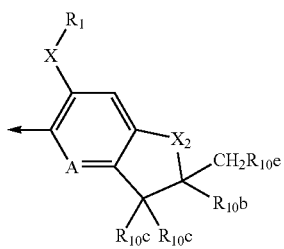
J₂₇
and A, R₁, R₂, X, R₁₀ₐ, R₁₀ᵦ, R₁₀c, R₁₀d, are as defined in claim 5, and X₂ is oxygen or S(O)n₁, wherein n₁ is 0, 1, or 2, and R₁₀ₑ is hydrogen, $C_1$-$C_6$alkyl, $C_1$-$C_6$haloalkyl, $C_3$-$C_6$cycloalkyl or $C_3$-$C_6$halocycloalkyl.
10. A compound of formula I-3a
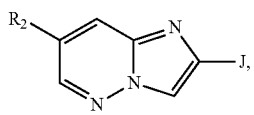
(I-3a)
wherein J is selected from the group consisting of
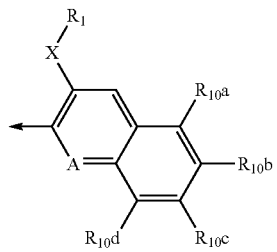
J₁
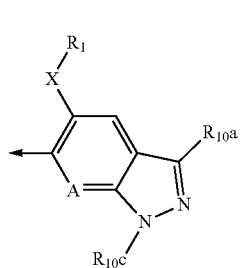
J₂
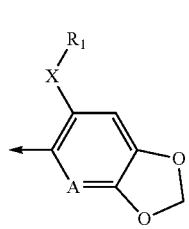
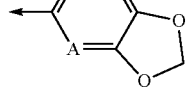
J₃
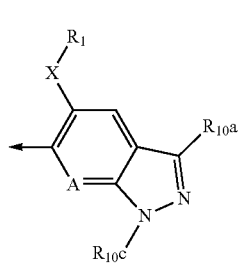
J₄
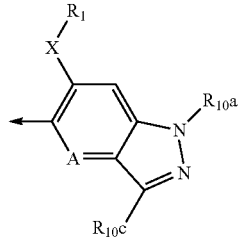
J₅
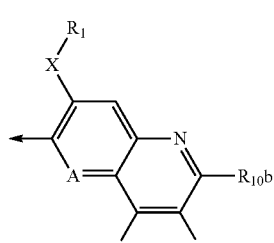
J₆
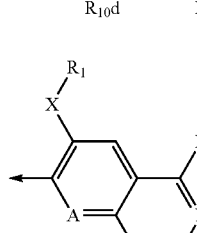

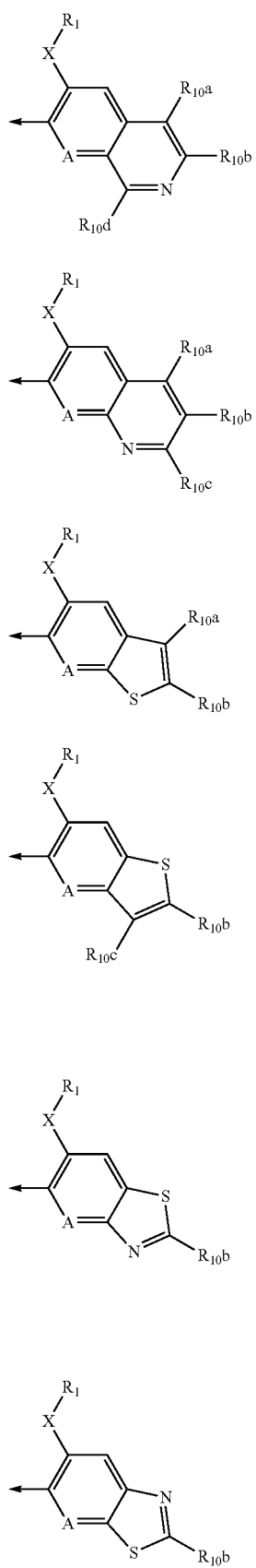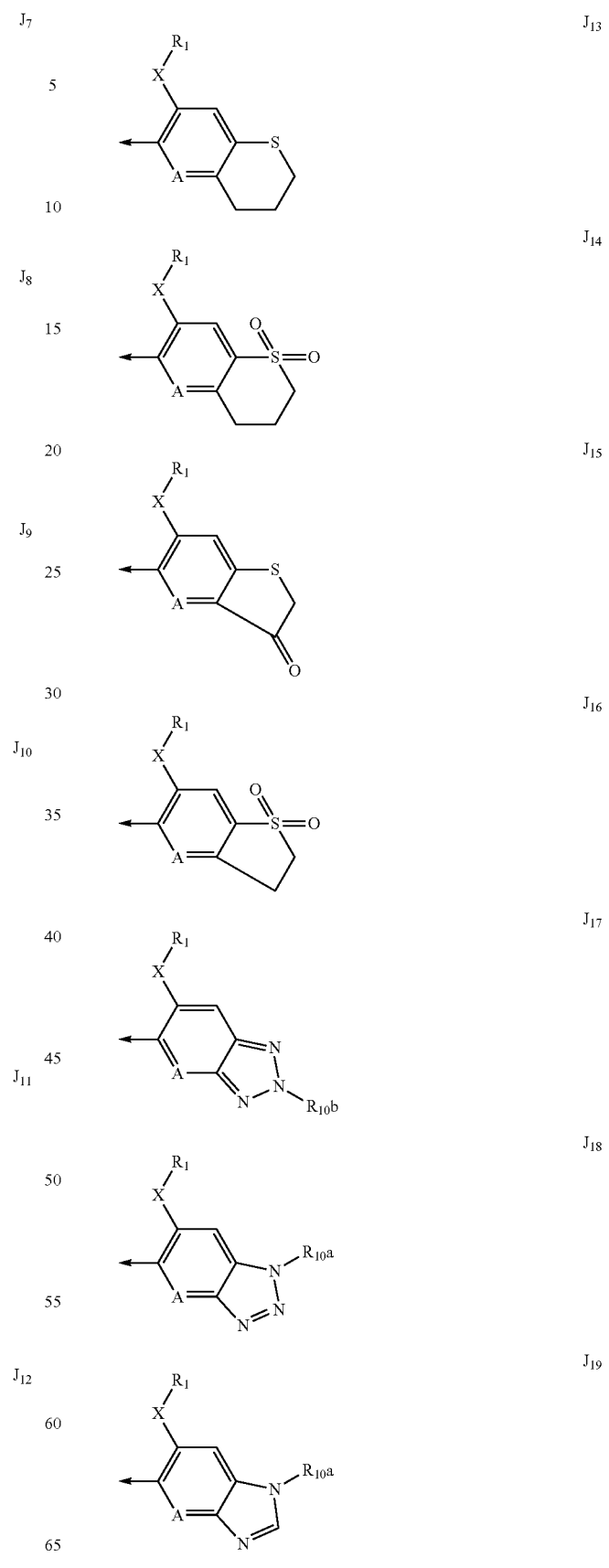

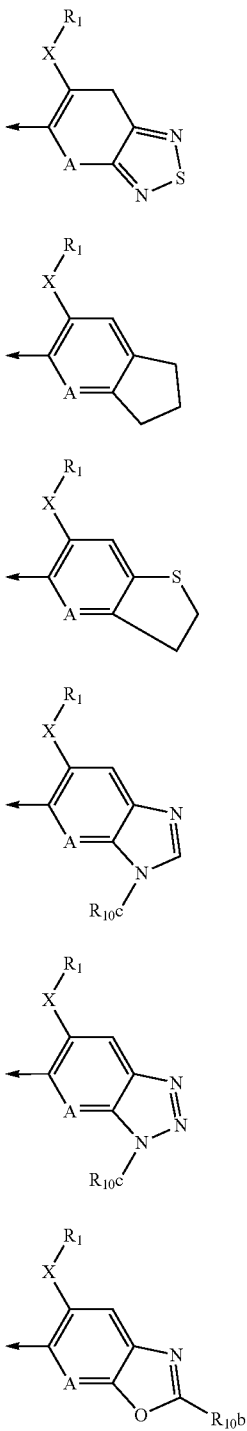

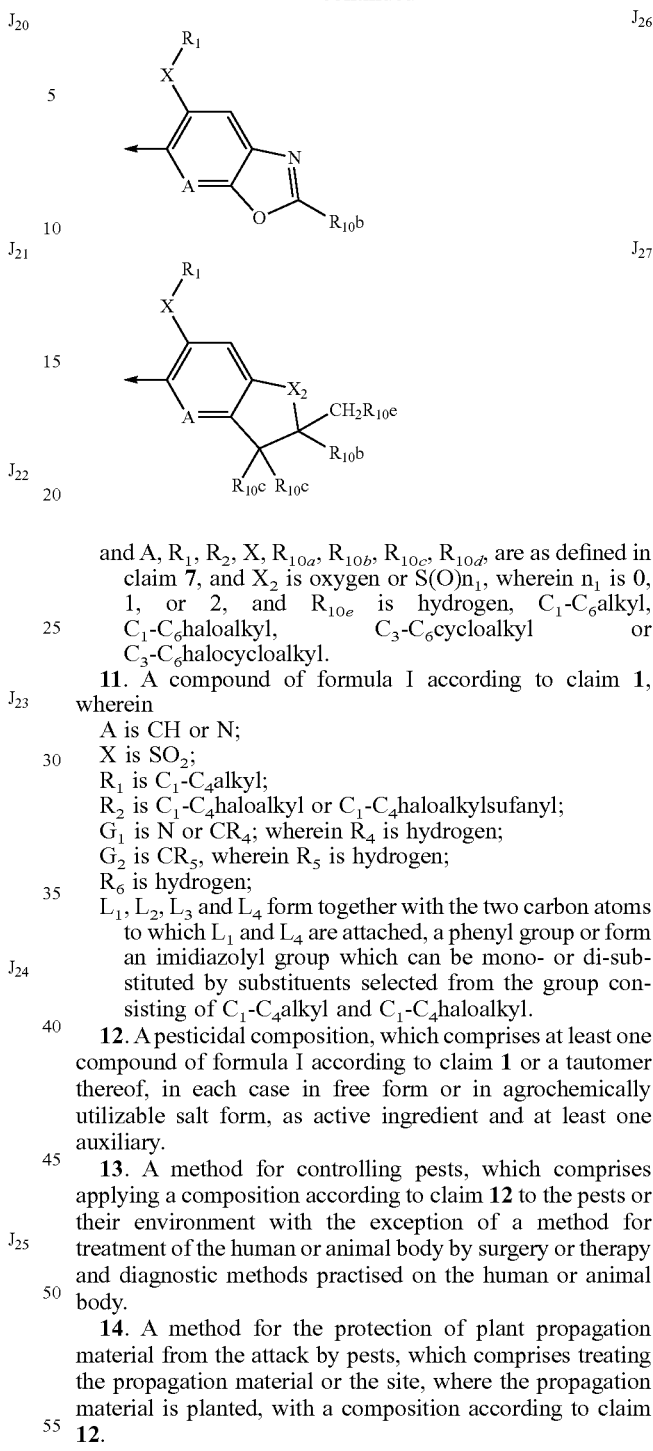

and A, $R_1$, $R_2$, X, $R_{10a}$, $R_{10b}$, $R_{10c}$, $R_{10d}$, are as defined in claim 7, and $X_2$ is oxygen or $S(O)n_1$, wherein $n_1$ is 0, 1, or 2, and $R_{10e}$ is hydrogen, $C_1$-$C_6$alkyl, $C_1$-$C_6$haloalkyl, $C_3$-$C_6$cycloalkyl or $C_3$-$C_6$halocycloalkyl.

11. A compound of formula I according to claim 1, wherein

A is CH or N;
X is $SO_2$;
$R_1$ is $C_1$-$C_4$alkyl;
$R_2$ is $C_1$-$C_4$haloalkyl or $C_1$-$C_4$haloalkylsufanyl;
$G_1$ is N or $CR_4$; wherein $R_4$ is hydrogen;
$G_2$ is $CR_5$, wherein $R_5$ is hydrogen;
$R_6$ is hydrogen;
$L_1$, $L_2$, $L_3$ and $L_4$ form together with the two carbon atoms to which $L_1$ and $L_4$ are attached, a phenyl group or form an imidiazolyl group which can be mono- or di-substituted by substituents selected from the group consisting of $C_1$-$C_4$alkyl and $C_1$-$C_4$haloalkyl.

12. A pesticidal composition, which comprises at least one compound of formula I according to claim 1 or a tautomer thereof, in each case in free form or in agrochemically utilizable salt form, as active ingredient and at least one auxiliary.

13. A method for controlling pests, which comprises applying a composition according to claim 12 to the pests or their environment with the exception of a method for treatment of the human or animal body by surgery or therapy and diagnostic methods practised on the human or animal body.

14. A method for the protection of plant propagation material from the attack by pests, which comprises treating the propagation material or the site, where the propagation material is planted, with a composition according to claim 12.

* * * * *